(12) United States Patent
Ladine et al.

(10) Patent No.: US 8,273,722 B2
(45) Date of Patent: Sep. 25, 2012

(54) ENHANCED BIOTHERAPEUTIC PRODUCTION USING INHIBITORY RNA

(75) Inventors: James R. Ladine, Whitinsville, MA (US); William S. Marshall, Boulder, CO (US); Yuriy Fedorov, Superior, CO (US); Christina Yamada, Boulder, CO (US)

(73) Assignee: Dharmacon, Inc., Lafayette, CO (US)

( * ) Notice: Subject to any disclaimer, the term of this patent is extended or adjusted under 35 U.S.C. 154(b) by 80 days.

(21) Appl. No.: 12/597,128

(22) PCT Filed: Jul. 11, 2008

(86) PCT No.: PCT/US2008/069859
§ 371 (c)(1),
(2), (4) Date: Mar. 19, 2010

(87) PCT Pub. No.: WO2009/012173
PCT Pub. Date: Jan. 22, 2009

(65) Prior Publication Data
US 2010/0173359 A1    Jul. 8, 2010

Related U.S. Application Data

(60) Provisional application No. 60/949,633, filed on Jul. 13, 2007.

(51) Int. Cl.
*C12N 15/11* (2006.01)
(52) U.S. Cl. .................................................. 514/44 A
(58) Field of Classification Search .................. 514/44 A
See application file for complete search history.

(56) References Cited

U.S. PATENT DOCUMENTS

| 6,586,206 | B1 * | 7/2003 | Dixit et al. | 435/69.1 |
| 2005/0074757 | A1 * | 4/2005 | Kreutzer et al. | 435/6 |
| 2005/0096284 | A1 * | 5/2005 | McSwiggen | 514/44 |
| 2005/0234232 | A1 * | 10/2005 | Beigelman et al. | 540/5 |
| 2008/0085869 | A1 * | 4/2008 | Yamada et al. | 514/44 |

OTHER PUBLICATIONS

Hacker et al. (Gene, 341:2004, 227-234).*
Arai et al. (Journal of Biochemistry 2004, 136, 421-425).*
Kuystermans et al. (Cytotechnology 2007, 53, 3-22).*
Czauderna et al. (Nucleic Acid Research 2003, 31, 2705-2716).*
Lim et al., RNA suppression of Bax and Bak enhances viability in fed-batch cultures of CHO cells, Metabolic Engineering 8 (2006) 509-522.
Weber, W. et al., "Inducible product gene expression technology tailored to bioprocess engineering," Current Opinion in Biotechnology, Oct. 2007, vol. 18, pp. 399-410.
International Search Report dated Feb. 20, 2009 cited in Application No. PCT/US2008/069859.

* cited by examiner

*Primary Examiner* — Brian Whiteman
(74) *Attorney, Agent, or Firm* — Workman Nydegger

(57) ABSTRACT

Compositions, kits, systems, equipment, and protocols utilize synthetic siRNA having a delivery facilitating moiety in improved bioprocesses that enhance the production of biomaterials. The siRNA can target genes associated with the following: 1) deleterious vector derived genes; 2) genes that confer non-optimal growth or differentiation properties to the cells; 3) genes that can influence heterogeneity or post-translational modification pattern of the desirable gene product; 4) genes that highly express non-desired proteins; 5) genes that express proteins which interfere with purification of the desired protein; and 6) other genes that can interfere with the bioprocess.

17 Claims, 9 Drawing Sheets

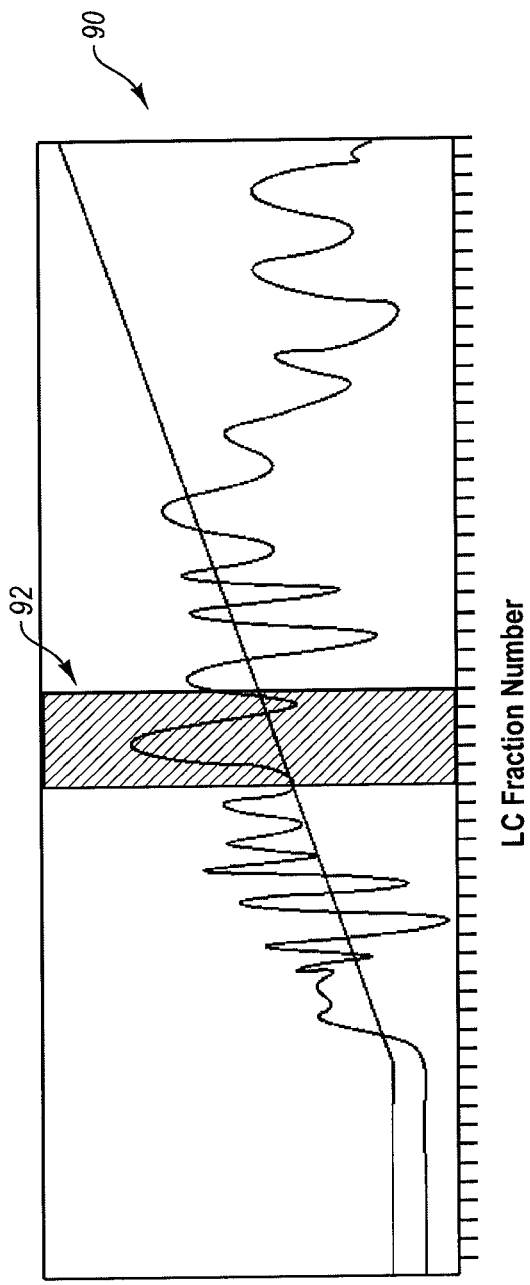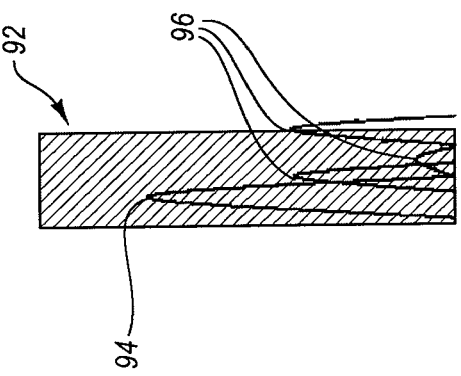

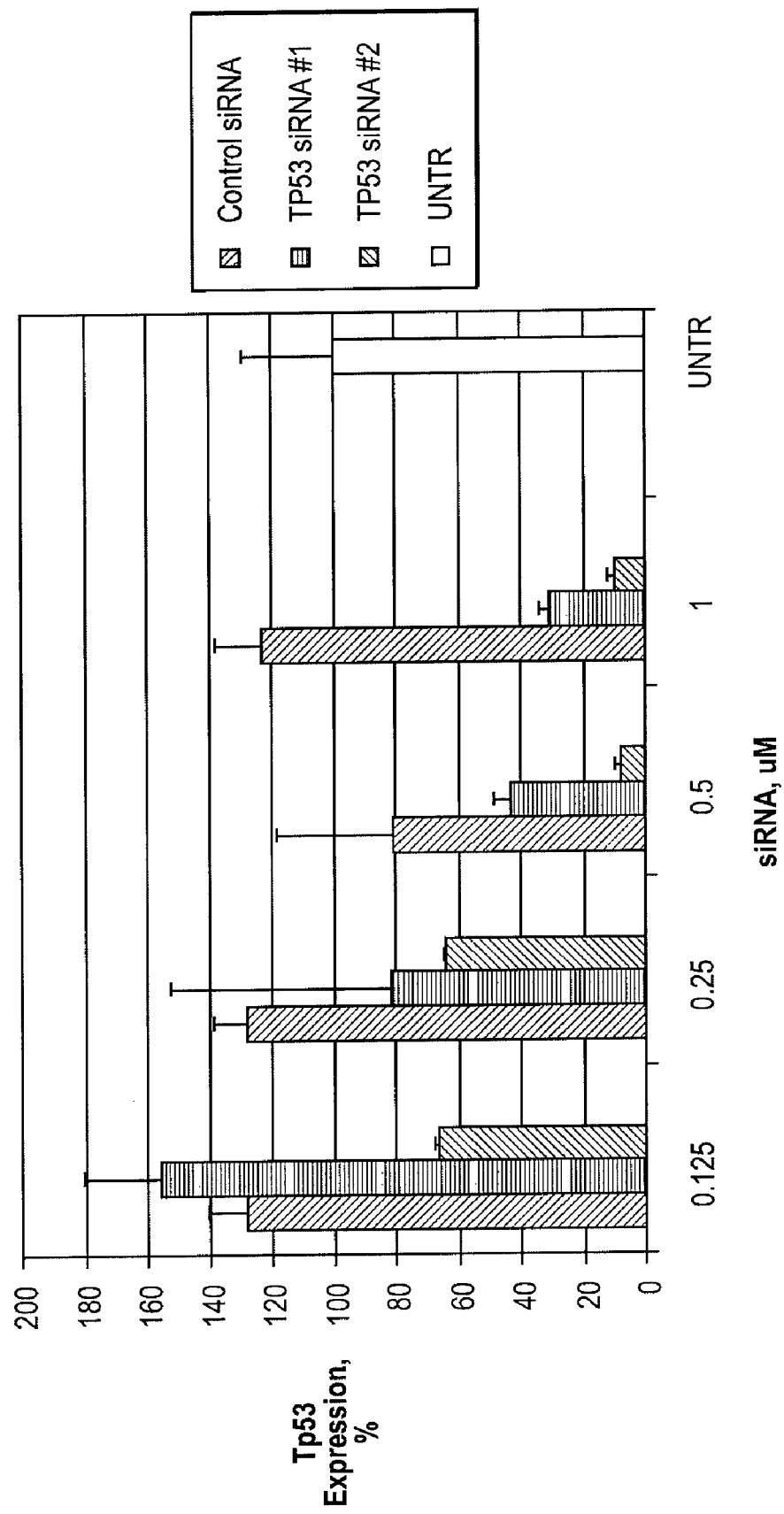

| Transfection: Time after transfection | UNTREATED | NTC siRNA | CASP3 siRNA |
|---|---|---|---|
| 72 hr | 1671048 +/- 33566 | 1810836 +/- 95288 | 1684622 +/- 46571 |
| 96 hr | 2413188 +/- 29605 | 2628746 +/- 18947 | 2042937 +/- 32603 |
| 120 hr | 2935595 +/- 107929 | 3325762 +/- 505203 | 2014424 +/- 45290 |

FIG. 6B

ENHANCED BIOTHERAPEUTIC PRODUCTION USING INHIBITORY RNA

CROSS-REFERENCE TO RELATED APPLICATIONS

This application is a United States nationalization of PCT/US2008/69859, which was filed 11 Jul. 2008 and entitled "ENHANCED BIOTHERAPEUTIC PRODUCTION USING INHIBITORY RNA." PCT/US2008/69859 claims the benefit of and priority to U.S. provisional patent application Ser. No. 60/949,633, filed Jul. 13, 2007. The above listed applications are incorporated herein in their entireties by specific reference.

BACKGROUND OF THE INVENTION

1. The Field of the Invention

The present invention relates to short interfering RNA (siRNA) that operate within the RNA interference (RNAi) pathway so as to enhance the production of industrially important polypeptides, especially biotherapeutic polypeptides and/or proteins. More particularly, synthetic siRNA that include a delivery facilitating moiety for cellular delivery and uptake can be used to enhance the production of biotherapeutic polypeptides by selectively silencing genes, a family of genes, or a biological pathway that have adverse effects on the production of the biotherapeutic polypeptides.

2. The Related Technology

Biotechnological innovations have resulted in a large number of therapeutic polypeptides (e.g., biotherapeutic agents) that are produced by recombinant nucleic acids being expressed within a cell. A primary goal of industrial producers of biotherapeutic agents is to obtain maximum yields of the polypeptide. As such, it is desirous to have cells which efficiently produce polypeptides that can be obtained in substantially pure, active, and homogeneous compositions and in quantities that are suitable for use as a biotherapeutic agent. Industrial producers of biotherapeutic agents continue to seek process improvements that allow the biotherapeutic agent to be obtained as an economically-feasible polypeptide product from the least costly configuration of cells, media, and equipment. Thus, various procedures have commonly been employed in order to optimize the production of biotherapeutic agents.

One of the procedures that has been used for increasing the efficiency of producing biotherapeutic agents is through biochemical optimization. Biochemical optimization can be considered any biochemical modulation that affects the biochemistry of the cells and/or cell cultures that are used to produce the biotherapeutic agents. Traditional biochemical optimization of cell culture bioprocesses has been used to produce therapeutic polypeptides (e.g., antibodies and other protein therapeutic agents) by modulating, and thereby optimizing the following: cell selection; cell culture conditions; cell growth media; cell culture duration; and cell growth media supplementation. These basic levers of optimization rely on fundamental nutrient biochemistry.

Another procedure that has been used for increasing the efficiency of producing biotherapeutic agents is through genetic optimization. Genetic optimization can be considered any genetic modulation that affects the genes and gene processing mechanisms of the host cells that produce the biotherapeutic agents. As such, genetically targeted modes of optimization have used the tools of molecular cloning to introduce targeted genetic alterations into the cell in order to increase expression of the desired product or to decrease the expression of genes that in any way could impair the yield of the desired biotherapeutic agent. Accordingly, genetic optimization can be employed by inserting specific sequences of DNA in the host cells or excising specific sequences of DNA therefrom in order to improve the production of the biotherapeutic agent. Such genetic optimization can be conducted by the following: regulated over-expression of apoptotic inhibitor proteins in order to decrease cell death (Van De Goor, J.; Improvement of Industrial Cell Culture Processes by Caspase-9 Dominant Negative and Other Apoptotic Inhibitors (2005) *Cell Engineering Volume* 4 Springer); DNA-based disruption of genes ("Knock-out") that are found or predicted to impair efficient expression for any of a variety of reasons (Pharkya P, Maranas C D; An optimization framework for identifying reaction activation/inhibition or elimination candidates for overproduction in microbial systems. Metab Eng. 2006 January; 8(1):1-13): co-expression ("Knock-in") of proteins that will increase expression of the desired protein, such as by agonizing or antagonizing regulatory pathways (Whitford, W.; Fed-Batch Mammalian Cell culture in Bioproduction. Bioprocess International April 2006: 31-40); and fusion of various affinity tags to the desired protein for the purpose of enhancing the speed and convenience of product purification (Hatti-Kaul, R., and Mattiasson, B.; (2003) *Isolation and Purification of Proteins: Chapter 4, Genetic Approaches to Protein Purification*. Marcel Dekker). Such affinity recognition elements include sequences from: immunoglobulin binding domains; repeating histidine residues; maltose binding protein, glutathione-S-transferase, and others.

While various optimization procedures have been employed in the bioproduction of biotherapeutic agents, industrial producers of biotherapeutic agents continue to seek still more optimization.

BRIEF SUMMARY

Generally, the present invention provides an improved bioprocess that optimizes the production of biomaterials (e.g., biotherapeutic agents) that are produced via bioprocessing. Additionally, the present invention provides an improved bioprocess that inhibits a biological pathway that can reduce the efficiency of producing biotherapeutic agents.

In one embodiment, a bioprocessing method for producing a protein-containing product from CHO cells can include the following: culturing recombinant host CHO cells containing a nucleic acid encoding at least a portion of the protein-containing product; contacting the recombinant host CHO cell with a synthetic, chemically modified siRNA having a delivery facilitating moiety conjugate linked to a polynucleotide of the siRNA under conditions in which the synthetic siRNA passively transfects the recombinant host CHO cell in an amount sufficient to inhibit expression of a first protein, wherein expression of the first protein decreases the production efficiency of the protein-containing product; incubating the recombinant host CHO cells with the synthetic siRNA under conditions that inhibit expression of the first protein; incubating the recombinant host CHO cells under conditions that express the protein-containing product; and recovering the protein-containing product. Optionally, both incubating steps can occur concurrently adjacently, or separately. The siRNA can be any siRNA described herein capable of being passively delivered into CHO cells.

In one embodiment, a bioprocessing method for producing a protein-containing product from host cells on an industrial scale can include the following: culturing recombinant host cells containing a nucleic acid encoding at least a portion of the protein-containing product, the host cells being present in the culture in an amount sufficient for an industrial scale bioprocess; contacting the recombinant host cells with a synthetic siRNA under conditions in which the synthetic siRNA passively transfects the recombinant host cell in an amount sufficient to inhibit expression of a first protein in the host cells, wherein expression of the first protein decreases the production efficiency of the protein-containing product; incubating the recombinant host cells with the synthetic siRNA under conditions that inhibit expression of the first protein; incubating the recombinant host cells under conditions that express the protein-containing product on an industrial scale; and recovering the protein-containing product. The siRNA can be any siRNA described herein capable of being passively delivered into cells which can be any cell type, such as CHO cells.

In one embodiment, a bioprocessing system for producing a protein-containing product can include: a recombinant host cell containing a nucleic acid encoding at least a portion of the protein-containing product; and an industrial scale amount of a synthetic siRNA that is configured to inhibit the expression of a first protein in an industrial bioprocess, wherein undesirable expression of the first protein decreases the production of the protein-containing product. The synthetic siRNA is a 19 base pair duplex and can include: a sense strand having 2'-O-methyl modifications on the ultimate and penultimate nucleotides (counting from the 5' end of the strand), 2'-O-methyl modifications on one or more pyrimidine nucleotides, and a cholesterol or cholesterol derivative conjugate coupled to the 3' end of the sense strand through a linker having a 3-member to 8-member carbon chain; and an antisense strand having 2'-fluorine modifications on one or more pyrimidines nucleotides, a 5' terminal phosphate, and a 3' overhang that includes one or more phosphorothioate internucleotide linkages. Optionally, the siRNA can include a mismatch at one or more nucleotides of the sense strand, where the mismatch can be at nucleotide 6, 14, and/or 18 counting from the 5' end of the sense strand. The mismatch(es) are between the sense and antisense strands but allow substantial complementarity to be retained between the antisense strand and the target mRNA.

In one embodiment, a recombinant host CHO cell for use in producing a protein-containing product can include: a nucleic acid encoding at least a portion of the protein-containing product; and synthetic siRNA configured to inhibit the expression of a first protein in an industrial bioprocess, wherein undesirable expression of the first protein decreases the production of the protein-containing product. The siRNA can be any siRNA described herein capable of being passively delivered into CHO cells or other cells substituted for the CHO cells.

Also, the present invention provides for siRNA to be used in a method of in vitro bioprocessing as opposed to in vivo methods (i.e., in cells). That is, the preparation of the biological material is performed with purified cellular proteins and/ or additional components derived from a cell. Such an in vitro manufacturing method constitutes a cell-free (e.g., in vitro translation) bioprocessing system. For example, the siRNA molecules can be introduced into cells to silence a target gene. These cells are later lysed and purified cellular fractions are then used for in vitro translation processes in order to generate the desired biological material. Alternatively, cells can be first lysed, and the siRNA molecule can be added directly to purified fractions of the cell-free extract to enhance production of the desired biological material. In vitro bioprocessing can be performed with siRNA that either include or exclude a delivery facilitating moiety.

These and other embodiments and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope.

FIGS. 4A and 4B include a chromatograph of elutant fractions of a protein-containing product and protein contaminates.

FIGS. 5A and 5B include graphs illustrating gene silencing in CHO cells with synthetic siRNA administered by passive delivery.

FIG. 6B includes a table showing gene silencing in CHO cells with passively delivered siRNA are effective in silencing a target gene.

DETAILED DESCRIPTION OF THE PREFERRED EMBODIMENTS

Figure 1:
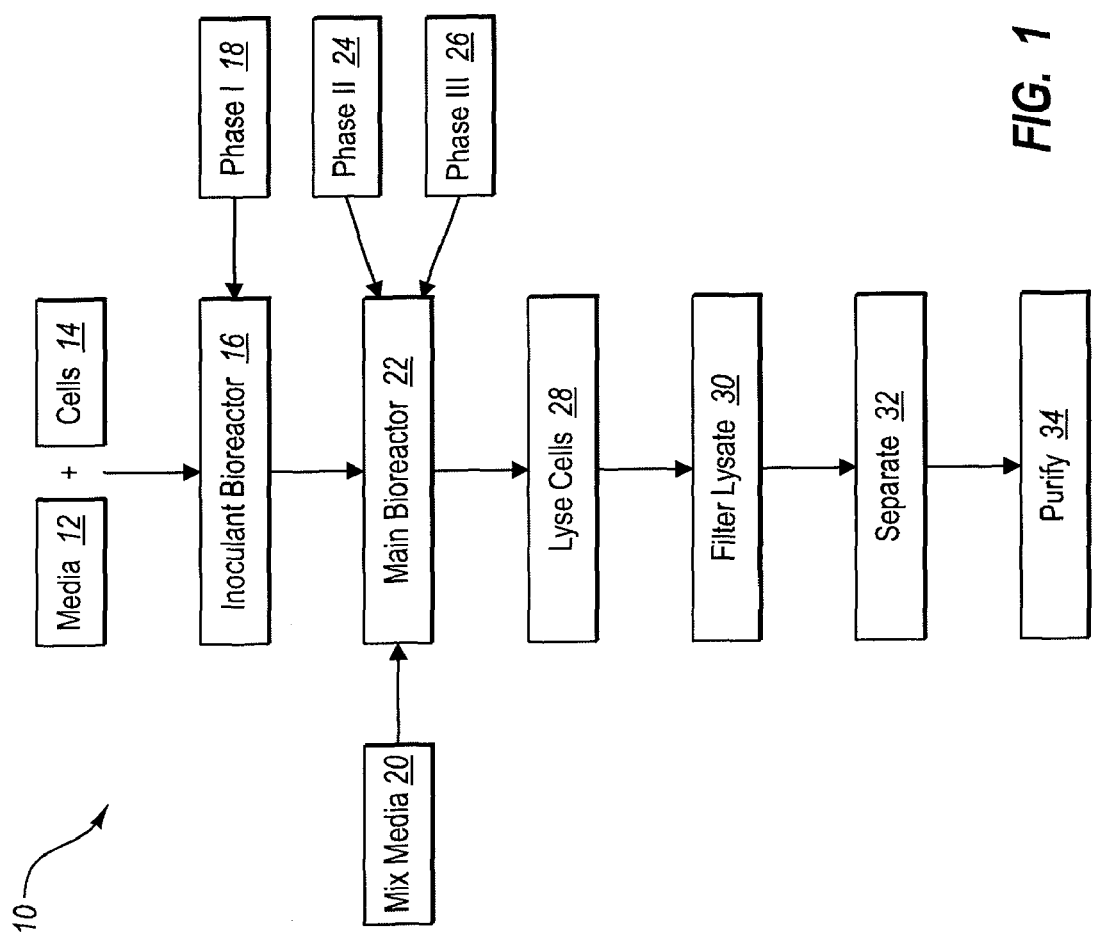
FIG. 1 is a schematic representation of an embodiment of a bioprocess and system.

Generally, embodiments of the present invention provide compositions, kits, systems, equipment, and protocols that utilize RNAi in improved bioprocesses that enhance the production of biomaterials (e.g., biotherapeutic agents, industrial intermediates, etc.). Additionally, the present invention provides improved bioprocesses that use siRNA, such as siRNA having a delivery facilitating moiety, in order to inhibit natural or artificial biological processes that can reduce the efficiency of producing the biomaterials. The siRNA can target genes associated with the following: 1) deleterious vector derived genes; 2) genes that confer non-optimal growth or differentiation properties to the cells; 3) genes that can influence heterogeneity or post-translational modification pattern of the desirable gene product; 4) genes that highly express non-desired proteins; 5) genes that express proteins which interfere with purification of the desired protein; and 6) other genes that can interfere with the bioprocess.

Bioprocesses of genetically modified (e.g., recombinant) host cells, such as CHO cells, is a growing industry that allows enhanced and cost-efficient production of desirable biotherapeutic agents and biological materials (e.g., industrial intermediates) that are used to make research and diagnostic reagents (e.g., protein receptors used in making kits for in vitro assays). It has now been found that siRNAs that have a delivery facilitating moiety, such as cholesterol covalently linked thereto, can be used to knockdown the expression of genes that decrease the efficiency of producing the biotherapeutic agents and other biomaterials in CHO cells. The siRNA having a cholesterol delivery facilitating moiety have now been shown to successfully knock down a target gene in CHO cells so as to alter the CHO cell phenotype. Such alteration of the CHO cell phenotype via transfection of synthetic siRNA via passive delivery through a delivery facilitating moiety can be used in bioprocessing in order to create a desired CHO phenotype that produces a desired biomaterial. Also, passive delivery can be implemented without a polynucleotide carrier, such as a lipid or cationic polymer, which is advantageous because polynucleotide carriers are toxic and can cause undesirable phenotypes in CHO cells. Undesirable changes in phenotypes can compromise the ability to successfully produce the desired biological material.

Accordingly, the following disclosure relates to compositions, kits, systems, equipment, and protocols for enhancing production of a biotherapeutic agent or other biological material by using siRNA having targeting moieties that passively deliver the siRNA into CHO cells so that the siRNA can operate within the RNAi pathway to silence genes that produce products that interfere with the production of the desired biological. The protocols can be implemented by treating cells with a gene silencing siRNA that is chemically synthesized and passively delivered in order to suppress the expression of proteins that interfere with the production, or purification of the desired biological material.

The compositions, kits, systems, equipment, and protocols for use thereof provide enhanced production of a biomaterial in a bioprocess that includes exposing a cell that produces the biomaterial to a gene silencing agent. The biomaterial is often a protein, which can be any protein capable of being produced in cells that has desirable properties. The cell in which it is made (e.g., host cell) can be an unmodified cell or cell line, or a genetically modified cell line (e.g., variant) such as a cell line that contains one or more expression constructs designed to enhance production of the desired protein. For example, the cell line can be a CHO cell line or modified CHO cell line.

The compositions, kits, systems, equipment, and protocols for use thereof provide enhanced production of a biomaterial in a bioprocess with cellular proteins without actually producing the biological material in a cell. The siRNA molecules can be introduced into cells to silence a target gene, and the cells are later lysed and purified fractions are then used for in vitro translation processes in order to generate the desired biological material. Alternatively, cells can be first lysed, and the siRNA molecule can be added directly to purified fractions of the cell-free extract to enhance production of the desired biological material.

Lipid mediated delivery of siRNA through lipid polynucleotide carriers has been commonly used in research applications. The use of lipid polynucleotide carriers as transfection reagents, if used in bioprocessing could cause complications and thereby not result in significant net improvements in the yield or quality of the desired biological material or improvements in the reliability of the entire bioprocess. Polynucleotide carriers have been found to be toxic to the host cells, such as CHO cells, so as to impair the ability of the host cell to successfully produce the desired biological material on an industrial level. Also, the polynucleotide carriers have caused adverse and unwanted changes in the phenotype of CHO cells so that the process is compromised. Changes in the phenotype of CHO cells is unwanted, and may affect the ability to achieve regulatory approval, such as approval by the FDA. Also, changes in the phenotype of CHO cells can be considered a glitch in the bioprocess that results in the obtained biological material to be unsatisfactory in a number of fronts, such as purity, consistency, yield, functionality, and the like.

Moreover, the use of polynucleotide carriers may require the CHO cell media to be totally replaced during the bioprocess so that the toxic polynucleotide carrier can be removed; however, the total removal of the CHO cell media necessarily also removed substances that the CHO cells secrete into the media which are important for cellular function and for successfully producing the desired biological material in a manner suitable for an industrial process. This may also alter the CHO cell phenotype in an undesirable manner.

Specific suggestions have been made in the prior art to use expressed siRNA for gene silencing and enhancing production of a desired biological material. Expressed siRNA are achieved by first introducing an expression vector (e.g., viral vector) into the CHO cells so that the cells produce the siRNA. However, this could usually result in the CHO cells producing viral proteins and/or having viral contaminants within the cells. Also, expressed siRNA may be difficult to accurately regulate because there could be variability in the uptake of the virus and expression of the siRNA, which could compromise the ability to accurately silence the target gene. Moreover, unintended or uncontrolled expression of the siRNA or viral protein at an inappropriate time, amount, or manner could compromise the CHO cells and alter the phenotype. Besides changes in the phenotype, the use of viral vectors to produce expressed siRNA could compromise the ability to achieve regulatory approval, such as approval by the FDA, for the bioprocessing of the desired biological material. For these reasons, while expressed siRNA is likely to be an effective strategy in some applications, an ability to provide synthetic siRNA instead (without the drawbacks associated with lipid-mediated transfection) can provide an effective strategy in other situations, including especially in the development of production processes. For example, siRNA conjugates according to the present invention can be used to identify which host cell genes should be silenced and when, or which combinations of host cell genes should be silenced in what sequence. Only after such testing has been completed and results analyzed might one decide that some (or all) of the genes to be silenced should be silenced using the expressed siRNA approach and only then create the appropriate expression vectors.

In order to overcome the problems in bioprocessing that are associated with the use of siRNA and implementation of gene silencing to enhance bioprocessing, the present invention provides a synthetic siRNA that includes a delivery facilitating moiety that can be successfully delivered into a cell to obtain the desired phenotype that produces the desired biological material in a manner sufficient for industrial applications. As shown in the experimental data contained herein, CHO cells can be successfully transfected via passive delivery of an siRNA conjugated to a delivery facilitating moiety that facilitates delivery into the CHO cells.

Accordingly, the present invention demonstrates the ability to use a delivery facilitating moiety, such as cholesterol or cholesterol derivative, in order to enhance gene silencing in CHO cells through synthetic siRNA conjugated to the delivery facilitating moiety. CHO cells are the predominant cell line used in bioprocessing, and as such, it would be advantageous to have successfully use gene silencing in order to achieve a desired phenotype that produces a desired biological material. As such, bioprocessing can be enhanced by selective gene silencing by introducing an siRNA having a delivery facilitating moiety at a selected time point within the bioprocess and against a selected target gene.

Additionally, the present invention demonstrates the ability of siRNA conjugated to a delivery facilitating moiety to actually induce a desired phenotype. This has been shown by selectively targeting specific genes that are associated with apoptosis for silencing with the siRNA conjugated to a delivery facilitating moiety. Apoptosis is only an example of a biological pathway that can be silenced, and was utilized because it is known to be one of the major biological pathways that disrupt bioprocesses and impair yields and cause other problems. However, the siRNA conjugated to a delivery facilitating moiety can be configured to silence other genes that may impair the ability to produce a desired biological material, or silence other genes in a manner that enhances the bioprocessing of the desired biological material.

In one example, an siRNA conjugated to a delivery facilitating moiety (e.g., siRNAdfm) can be used to target genes that negatively affect cell viability. Specifically, siRNAdfm can be passively introduced into cells to target proapoptotic genes such as Casp3, and thereby enhance bioproduction by improving overall cell viability. Accordingly, CHO cells capable of producing a desired bioproduct are first treated with siRNAdfm targeting Casp3 at concentrations between 0.1 and 2 micromolar for 1-3 days. These cells are then introduced into a bioreactor at desired cell densities, and maintained as batch or batch-fed cultures whose apoptotic pathways are suppressed and therefore are capable of providing enhanced yields of the biomolecule.

In another example, siRNAdfm are used to target genes that negatively affect the stability of an mRNA transcript. Specifically, siRNAdfm can be passively introduced into cells to target genes that play a role in mRNA decay (e.g. KSRP) and thereby enhance bioproduction by extending transcript stability. Accordingly, CHO cells capable of producing a desired bioproduct are first treated with siRNAdfm targeting one or more genes associated with mRNA decapping (e.g., DCP1:DCP2 decapping complexes) at concentrations between 0.1 and 2 micromolar for 1-3 days. These cells are then introduced into a bioreactor at desired cell densities and maintained as batch or batch-fed cultures. As mRNA degradation is suppressed in these cells, enhanced yields of the biomolecule are expected.

In another example, siRNAdfm are used to target genes that repress translation. Specifically, siRNAdfm can be passively introduced into cells to target genes that play a role in translation repression or attenuation, and thereby enhance bioproduction by improving the translation of the desired transcript. Accordingly, CHO cells capable of producing a desired bioproduct are first treated with siRNAdfm targeting one or more genes associated with the RNAi pathway (e.g. members of RISC) at concentrations between 0.1 and 2 micromolar for 1-3 days. These cells are then introduced into a bioreactor at desired cell densities and maintained as batch or batch-fed cultures whose RNAi pathway is suppressed. As a result of these treatments, endogenous miRNAs are incapable of targeting the mRNA of interest and overall bioproduction would be enhanced.

In another example, siRNAdfm can be used to target genes that negatively affect the purification of the bioproduct. Specifically, siRNAdfm can be passively introduced into cells to target genes that aggregate with the bioproduct of interest, or co-purify with the bioproduct of interest. Accordingly, CHO cells capable of producing a desired bioproduct are first treated with siRNAdfm targeting a contaminant gene at concentrations between 0.1 and 2 micromolar for 1-3 days. These cells are then introduced into a bioreactor at desired cell densities and maintained as batch or batch-fed cultures. In these cases, subsequent purity of the bioproduct of interest is enhanced due to the absence of the contaminant protein.

Optimally, the foregoing examples are performed with siRNA conjugated to a cholesterol or cholesterol derivative for enhanced delivery of the siRNA into the CHO cells. This siRNAdfm can include a cholesterol conjugated to the siRNA via a linker as described herein.

Accordingly, the present invention includes a method for producing a polypeptide-containing product via bioprocessing through the use of synthetic siRNA that silence a target gene so as to enhance production of the polypeptide-containing product. Such a method includes the following: culturing a recombinant host cell, such as a CHO cell, containing nucleic acid encoding at least a portion of the protein-containing product; contacting the recombinant host cell with a synthetic siRNA having a delivery facilitating moiety under conditions in which the synthetic siRNA passively transfects the recombinant host cell and inhibits the expression of a first polypeptide, wherein undesirable expression of the first polypeptide decreases the production of the polypeptide-containing product; incubating the recombinant host cell with the synthetic siRNA under conditions that allow cell replication and expression of the polypeptide-containing product; and recovering the polypeptide-containing product from the recombinant host cell. In some instances the first polypeptide is an undesirable polypeptide (e.g., protein) that has deleterious effects on producing the polypeptide-containing product (e.g., protein-containing product). In other instances, the first polypeptide is the polypeptide of the polypeptide-containing product, which is expressed at an undesirable stage in the bioprocess, such as in Phase I.

The first polypeptide can be expressed from a DNA sequence cloned into the recombinant host cell with the nucleic acid encoding for at least a portion of the polypeptide-containing product. Optionally, the first polypeptide can be expressed from DNA endogenous to the host cell before recombination. In another option, the synthetic siRNA contacts the recombinant host cell prior to incubating the recombinant host cell in a bioreactor. In yet another option, the recombinant host cell is incubated for a first time period in a bioreactor, is then contacted with the synthetic siRNA, and is then incubated for a second time period in a bioreactor. In still another option, the method includes the following: incubating the recombinant host cell for a first time period in a bioreactor in the absence of the synthetic siRNA; contacted with the synthetic siRNA in a bioreactor; and incubating the recombinant host cell for a second time period in a bioreactor.

Additionally, the method can include inhibiting the production of the first polypeptide so as to enhance bioproduction of the polypeptide-containing product compared to instances wherein production of the first polypeptide is not inhibited. Also, the method also includes the following: inhibiting expression of the first protein during a first portion of the step of incubating the recombinant host cell while the recombinant host cell is replicating; and expressing the protein-containing product during a second portion of incubating the recombinant host cell after RNA interference activity of the transfected siRNA has been diminished.

Examples of the types of genes and/or biological pathways that can be silenced with the siRNAdfm can include at least one of the following: inhibiting fucosyl transferase; inhibiting caspases to inhibit apoptosis; silencing cell cycle progression genes to inhibit cell proliferation; silencing pro-senescence genes to inhibit host cell death; silencing calcium transporter genes to limit cross links; silencing a gene encoding CD16(Fc)(RIII) to prohibit aggregation; silencing genes encoding factors that destabilize transcriptions and/or affect translation; or silencing genes encoding factors associated with glycosylation of proteins.

Often, the first polypeptide that is silenced is a first protein and the polypeptide-containing product is a protein containing product. As such, descriptions of the invention that refer to polypeptides should also be construed to referring to proteins unless stated otherwise, and vice versa. Examples of the first protein can include at least one of the following: a vector protein that is deleterious to cell viability; a vector protein that is deleterious to production of the protein-containing product; a protein that is expressed at a particular stage of a bioprocess that is deleterious to the growth of the recombinant host cell; a protein that is expressed in Phase I of a bioprocess; a protein that is expressed in Phase II of a bioprocess; a protein that is expressed in Phase III of a bioprocess (as shown in FIG. 1); a protein that modifies the protein-containing product into an undesired form; a protease; a glycosylase; a kinase; a phosphatase; a protein that post-translationally modifies the protein-containing product; a protein that is over-expressed; a protein that is highly expressed so as to be deleterious to the expression of the protein-containing product; a protein that causes degradation of the protein-containing product; an ubiqutinase; a protein that associates with the protein-containing product; a protein that has substantially the molecular weight of the protein-containing product; a protein that has substantially the isoelectric point of the protein-containing product; a protein that has substantially the purification properties of the protein-containing product; a protein that interferes with recovering the protein-containing product; a protein that co-elutes with the protein-containing product; a viral protein; a protein having an activity that introduces a substantial structural heterogeneity into the protein-containing product; a fucosyl transferase; a caspase; a calcium transporter; CD16(Fc)(RIII); a protein that is difficult to separate from the protein-containing product during the step of recovering the protein-containing product; a protein that inhibits the growth or division of the recombinant host cell; a protein that restricts the expression of the protein-containing product; or a protein that post-translational modifies the protein-containing product into an undesired form.

A. Definitions

The following terminology is defined herein to clarify the terms used in describing embodiments of the present invention and is not intended to be limiting. As such, the following terminology is provided to supplement the understanding of such terms by one of ordinary skill in the relevant art.

As used herein, "antisense strand" is meant to refer to a polynucleotide or region of a polynucleotide that is at least substantially (e.g., about 79% or more) or 100% complementary to a target nucleic acid of interest. Also, the antisense strand of a dsRNA is substantially complementary to its sense strand. An antisense strand may be comprised of a polynucleotide region that is RNA, DNA, or chimeric RNA/DNA. Additionally, any nucleotide within an antisense strand can be modified by including substituents coupled thereto, such as in a 2' modification. The antisense strand can be modified with a diverse group of small molecules and/or conjugates. For example, an antisense strand may be complementary, in whole or in part, to at least a portion of a molecule of messenger RNA ("mRNA"), an RNA sequence that is not mRNA including non-coding RNA (e.g., tRNA and rRNA), or a sequence of DNA that is either coding or non-coding. The terms "antisense strand" and "antisense region" are intended to be equivalent and are used interchangeably. The antisense strand is also sometimes referred to as the guide strand in certain publications.

Perfect complementarity or 100% complementarity refers to the situation in which each nucleotide unit of one polynucleotide strand can hydrogen bond with a nucleotide unit of an anti-parallel polynucleotide strand. Less than perfect complementarity refers to the situation in which some, but not all, nucleotide units of two strands can hydrogen bond with each other. For example, for two 20-mers, if only two base pairs on each strand can hydrogen bond with each other, the polynucleotide strands exhibit 10% complementarity. In the same example, if 18 base pairs on each strand can hydrogen bond with each other, the polynucleotide strands exhibit 90% complementarity. "Substantial complementarity" refers to polynucleotide strands exhibiting 79% or greater complementarity, excluding regions of the polynucleotide strands, such as overhangs, that are selected so as to be non-complementary. Accordingly, complementarity does not consider overhangs that are selected so as not to be similar or complementary to the nucleotides on the anti-parallel strand.

As used herein, "conjugate" is meant to refer to a molecule that is coupled with the sense strand and/or antisense strand of an siRNA. That is, the moiety coupled to the siRNA is considered the conjugate. For clarity purposes, the siRNA can include a conjugate that is coupled thereto by a covalent bond, ionic interaction, and like couplings. Usually, a conjugate is coupled with an siRNA in order to impart a functionality other than increasing the stabilization or gene targeting specificity. For examples, some conjugates, such as cholesterol, can be used to enhance the ability of the siRNA to enter a cell. Other conjugates can be labels that are used to detect transfection or the presence of the siRNA in the cell. The conjugate can be coupled to the siRNA through a linker group. The choice of the linker group can be made from a wide variety of hydrocarbons, ring structures or hetero atom structures and can play an important role in the passive uptake of the siRNA molecule.

As used herein, "duplex" or "duplex region" is meant to refer to a molecule or the region in two complementary or substantially complementary polynucleotides that form base pairs with one another, either by Watson-Crick base pairing or any other manner that allows for a stabilized duplex between the polynucleotide strands. For example, a polynucleotide strand having 21 nucleotide units can base pair with another polynucleotide of 21 nucleotide units, yet only 19 bases on each strand are complementary such that the "duplex region" has 19 base pairs. The remaining bases may, for example, exist as 5' and/or 3' overhangs. Further, within the duplex region, 100% complementarity is not required, and substantial complementarity is allowable within a duplex region. Substantial complementarity refers to 79% or greater complementarity and can result from mismatches and/or bulges. For example, a single mismatch in a duplex region consisting of 19 base pairs results in 94.7% complementarity, rendering the duplex region substantially complementary.

As used herein, "functionality" is meant to refer to the level of gene specific silencing induced by an siRNA. In general, functionality is expressed in terms of percentages of gene silencing. Thus, 90% silencing of a gene (e.g., F90) refers to situations in which only 10% of the normal levels of gene expression are observed. Similarly, 80% silencing of a gene (e.g., F80) refers to situations in which only 20% of the normal levels of gene expression are observed.

As used herein, "gene silencing" is meant to refer to a process by which the expression of a specific gene product is inhibited by being lessened, attenuated, and/or terminated. Gene silencing can take place by a variety of pathways. In one instance, gene silencing can refer to a decrease in gene product expression that results from the RNAi pathway, wherein an siRNA acts as part of a multiprotein complex known as the RNA Induced Silencing Complex (RISC) to degrade mRNA in a sequence-dependent manner. Alternatively, gene silencing can refer to a decrease in gene product expression that results from siRNA mediated translation inhibition. In still another alternative, gene silencing can refer to a decrease in gene product expression that results from siRNA mediated transcription inhibition. The level of gene silencing can be measured by a variety of methods, which can include measurement of transcript levels by Northern Blot Analysis, B-DNA techniques, quantitative PCR analysis, transcription-sensitive reporter constructs, expression profiling (e.g., DNA chips), and related technologies and assays. Alternatively, the level of gene silencing can be measured by assessing the level of the protein encoded by a specific gene that is translated from the corresponding mRNA. This can be accomplished by performing a number of studies including Western Analysis, ELISA, measuring the levels of expression of a reporter protein, such as colorimetric or fluorescent properties (e.g., GFP), enzymatic activity (e.g., alkaline phosphatases), or other well known analytical procedures. Under the present invention, the silenced gene usually produces a protein that interferes with the production or purification of the desired protein product.

As used herein, "off-target" and "off-target effects" are meant to refer to any instance where an siRNA, such as a synthetic siRNA or shRNA, is directed against a given target mRNA, but causes an unintended effect by interacting either directly or indirectly with another mRNA, a DNA, a cellular protein, or other moiety in a manner that reduces non-target protein expression. Often, this can happen when an siRNA interacts with non-target mRNA that has the same or similar polynucleotide sequence as the siRNA. For example, an "off-target effect" may occur when there is a simultaneous degradation of other non-target mRNA due to partial homology or complementarity between that non-target mRNA and the sense and/or antisense strand of the siRNA.

As used herein, "on-target" is meant to refer to a set of modifications of an siRNA that increase the likelihood that the siRNA will preferentially target and interact with a target mRNA or DNA so as to inhibit production of the polypeptide encoded thereby. This increases the specificity of the siRNA for silencing the target gene. For example, an on-target modification can include a siRNA where the first and second nucleotides of the sense strand each has a 2'-O-methyl moiety, and the antisense strand is phosphorylated at its 5' end, wherein such an on-target modification also refers to a proprietary modification coined On-Target™(Dharmacon, Inc.). Additionally, on-target modifications can include a siRNA wherein the first and second strands have 2'-O-methyl modifications at the first and/or second nucleotides from the 5' ends, which is also referred to as the proprietary modification coined "OTP" (Dharmacon, Inc.). In any event, on-target modifications can be used to help reduce off-target effects. Also, an siRNA can have a sense strand that has exact or substantial complementarity to the antisense strand of the siRNA, and wherein the antisense strand has exact or substantial complementarity to a target mRNA.

As used herein, "passive delivery" is meant to refer to the process where a polynucleotide, such as siRNA or siRNA precursor is delivered to a cell without a transfection reagent. That is, a transfection reagent is not combined with the polynucleotide prior to administration to the cell. As such, passive delivery does not utilize a transfection cocktail (e.g. lipofectaine 2000, DharmaFECT, etc.). However, passive delivery does include the polynucleotide having a conjugate that can facilitate gene delivery, such as a cholesterol conjugate. Generally, passive delivery does not utilize external means separate from the siRNA to enhance transfection.

As used herein, "siRNA pool," "pool," "pool of siRNAs," and "pool reagents" are meant to refer to two or more siRNA, typically four siRNA, directed against a single target gene, mRNA, and/or translation of a protein. The siRNA of the pool reagent can be rationally designed by being selected according to non-target specific criteria. For example, two nanomoles of each pool reagent can be sufficient for transfecting cells in about 200 wells of multiple 96-well plates, using 100 nM siRNA concentration. Pool reagents can be plated as a pool (i.e., the two or more siRNA of Dharmacon's SMARTpool® Reagent in a single transfection well). The individual siRNAs that comprise the SMARTpool® Reagent, sometimes referred to herein as SMARTselection™ siRNA (Dharmacon, Inc.), can also be plated individually on the same plate as the SMARTpool® Reagent. Accordingly, pools of siRNA can be prepared to target and silence a gene encoding for a protein that interferes with the production or purification of the desired protein product.

As used herein, "target" is used in a variety of different forms throughout this document and is defined by the context in which it is used. The term "target gene" is meant to refer to the gene that encodes a protein that interferes with the bioprocess and that needs to be silenced by the siRNA. The term "target mRNA" is meant to refer to an mRNA (e.g., encoded by the target gene) against which a given siRNA is direct to silence the expression of the target protein that interferes with the bioprocess. The term "target sequence" and "target site" are meant to refer to a sequence within the mRNA, miRNA, or DNA coding or promoter region to which the sense strand of an siRNA exhibits varying degrees of homology and the antisense strand exhibits varying degrees of complementarity. The term "target polypeptide" or "target protein" is meant to refer to the gene product encoded by the target gene, target mRNA, and/or target sequence that interferes with the bioprocess. The term "siRNA target" can refer to the gene, mRNA, or protein against which the siRNA is directed to for silencing. Similarly, "target silencing" can refer to the state of silencing a gene, or the corresponding mRNA or protein.

As used herein, the term "transfection" is meant to refer to a process by which nucleic acids are introduced into a cell. The list of nucleic acids that can be transfected is large and includes, but is not limited to, siRNA, shRNA, miRNA, piRNA, pre-miRNA, sense and/or anti-sense sequences, DNA, RNA, and the like. There are multiple modes for transfecting nucleic acids into a cell including, but not limited to, electroporation, particle bombardment, calcium phosphate delivery, DEAE-dextran delivery, lipid delivery, polymer delivery, molecular conjugate delivery (e.g., polylysine-DNA or -RNA conjugates, antibody-polypeptide conjugates, antibody-polymer conjugates, or peptide conjugates), microinjection, laser- or light-assisted microinjection, optoporation or photoporation with visible and/or nonvisible wavelengths of electromagnetic radiation, and the like. Transfections can be "forward transfections" whereby cells are first cultured and then treated with a nucleic acid or they can be "reverse transfections" (RTF) whereby the nucleic acid is combined with the cells before or during being introduced into a culture environment. See the above definition of passive delivery for a preferred set of transfection methodologies.

As used herein, "variant cell" is meant to refer to any "variant" of a specified cell line including progeny of the specified cell line, a modified or mutated cell line obtained or derived from the specified cell line or its progeny, or other recipient cell line that contains genetic material obtained directly or indirectly from the specified cell line. Such a variant cell line may, for example, be formed by removing genetic material from a specified microorganism or cell line and subsequently introducing it into a cell line (i.e., the progeny or other recipient cell line) by any conventional methodology. A variant may be formed by introducing one or more mutations or modifications into the genome or other genetic material (e.g., vectors, plasmids, extrachromosomal elements, etc.) of a cell line. Such mutations or modifications may include one or more insertion mutations, deletion mutations and/or substitutions or various combinations thereof. The mutations or modifications may be insertions into the genome or other genetic material (e.g., vectors, plasmids, extrachromosomal elements, etc.) of the cell line. Alternatively, the mutations may be deletions of one or more bases and/or nucleic acid sequences from the genome or other genetic material (e.g., vectors, plasmids, extrachromosomal elements, etc.) of the cell line. In some instances, the mutations may be the alteration of one or more bases in the genome of the cell line. Such modifications or mutations may also comprise, for example, methylating or possibly substituting one or more nucleic acid bases and/or nucleic acid molecules for other nucleic acid molecules and/or bases. In addition, one cell line is a variant of a parent cell line if it contains the genome of the parent cell line but does not contain some or all of the same extrachromosomal nucleic acid molecules. Variants of a cell line of the invention may also include those cell lines obtained by the addition of one or more nucleic acid molecules into the cell line of interest. Nucleic acid molecules which may be introduced into a cell line will be recognized by one skilled in the art and may include, but are not limited to, vectors, plasmids, oligonucleotides, RNA, DNA, RNA/DNA hybrids, phage sequences, virus sequences, regardless of the form or conformation (e.g., linear, circular, supercoiled, single stranded, double stranded, single/double stranded hybrids and the like). Examples of mutations or other genetic alterations which may be incorporated into the cell line of the present invention include, but are not limited to, mutations or alterations that create: a cell line resistant to antibiotic selection, a cell line with increased permissiveness to transfection; a cell line with increased expression of transgenes; genomic incorporation of a gene of interest in a cell line; and genomic incorporation and amplification of a gene of interest in a cell line. Other suitable modifications are known to those skilled in the art and such modifications are considered to be within the scope of the present invention. Variant cells can be advantageous in the bioprocesses of the present invention.

As used herein, "vector" refers to a plasmid, phagemid, cosmid, virus or phage nucleic acid or other nucleic acid molecule that is able to replicate autonomously or to be replicated in a host cell. Preferably a vector is characterized by one or a small number of restriction endonuclease recognition sites at which such nucleic acid sequences may be cut in a determinable fashion without loss of an essential biological function of the vector, and into which nucleic acid molecules may be spliced in order to bring about replication and cloning. The cloning vector may also utilize defined recombination sites to allow for the integration of the gene in the absence of restriction digest. An example of such system is the Gateway Vector (Invitrogen). The cloning vector may further contain one or more markers suitable for use in the identification of cells transformed with the cloning vector. Markers, for example, are antibiotic resistance genes including, but not limited to tetracycline or ampicillin resistance, hygromycin B or neomycin resistance; and/or fluorophores, including, but not limited to green fluorescent protein or beta-lactamase.

The use of units to define measurable quantities of material, such as concentration, weight, and volume, are intended to be those that are routinely employed by those of skill in the art. Additionally, the units are preferably interpreted to correspond with the metric system. Also, the use of "u," as in "ug" or "uL" is meant to refer to "micro" as applied to microgram and microliter, respectively.

Additionally, while the foregoing term definitions are intended to supplement the knowledge of one of ordinary skill in the art, not every term within this document has been defined. As such, the undefined terms are intended to be construed with the knowledge of one of ordinary skill in the art and/or the plain meaning of the term. Additionally, the foregoing terms are not intended to be limited by the examples provided therein, but are intended to be useful in understanding and practicing the invention as described herein.

Furthermore, the definitions provided in the following references are incorporated herein by specific reference: U.S. Provisional Patent Application Ser. Nos. 60/949,633, 60/542, 668 and 60/543,661; U.S. patent application Ser. No. 10/406, 908, filed Apr. 2, 2003, published as U.S. Patent Application No. 2004/0198640; U.S. patent application Ser. No. 10/613, 077, filed Jul. 1, 2003, published as U.S. Patent Application No. 2004/0266707 A1 on Dec. 30, 2004; and in PCT/US04/10343, international filing date Apr. 1, 2004, published as WO 2004/090105 A2 on Oct. 21, 2004.

I. Bioprocessing

Bioprocessing includes the use of biological materials (e.g., organisms, cells, organelles, enzymes, proteins, antibodies, glycoproteins, cell products, and the like) to carry out a process for producing a biological product. The biological product can be a biotherapeutic agent, such as a polypeptide, protein, enzyme, metabolite, or the like. Often, bioprocessing is implemented in order to produce materials for use in other industrial applications or as endpoint products. Two exemplary bioprocessing products are erythropoietins (Aranesp, Epogen, Procrit, Eprex) and anti-TNF binding proteins (Enbel, Remicade, Humira) that have commercial applications.

Additionally, there are many different types of systems and protocols for implementing a bioprocess, and describing each type of bioprocess with regard to the present invention would be cumbersome. While some systems are configured for batch processing, others are configured for continuous or steady-state processing. However, the features of the present invention are equally applicable to batch, continuous, and steady-state bioprocessing applications. As such, representative bioprocesses and associated systems and protocols described herein can be easily adapted and/or modified so as to be usable for other bioprocesses, thereby resulting in essentially any bioprocess to utilize the features of the present invention.

FIG. 1 is a schematic illustration of a generic bioprocess 10 for producing an intracellular protein product. In the illustrated bioprocess, media 12 and cells 14 (e.g., eukaryotic, such as CHO) are introduced into an innoculant bioreactor 16, and the cells 14 are grown to an appropriate level. As such, the media 12 introduced into the innoculant bioreactor 16 can be configured to enhance cell growth. This can also include configuring the media 12 to reduce production of the desired protein product. The duration where the cells 14 are grown in the innoculant bioreactor 16 can be considered to be Phase I 18.

Often, the cells 14 are then removed from the innoculant bioreactor 16 and placed in the main bioreactor 22 with a mixed media 20. However, a single bioreactor can be used instead of the innoculant bioreactor 16 and main bioreactor 22 combination. The early phase of cell growth in the main bioreactor 22 can be enhanced similarly as in the innoculant bioreactor 16 so that the cells 14 have optimal growth. Again, the cell culture media (e.g., mixed media 20) can be configured to optimize cell growth and reduce the production of the desired protein, such as a glycoprotein. The initial phase of cell growth in the main bioreactor 22 can be considered to be Phase II 24.

After the initial cell growth period in the main bioreactor 22, the cells 14 can then produce the desired protein product, such as a glycoprotein. Usually, there is a shift from a growth mode to a product production mode, which can be induced by adding various components to the media, such as metabolites that promote expression of genes downstream of appropriate promoter sequences. The shift can be monitored so that the duration of protein product production can be determined. Also, the shift can occur naturally as part of the natural cell cycle, and can coincide with the cells dividing less than in the growth phase. Alternatively, there are systems in which a slight shift in the temperature of the cell culture vessel causes induction of the expression of the desired protein. The phase of protein product production in the main bioreactor 22 can be considered to be Phase III 26.

After the protein product is produced within the cells 14 in a sufficient amount or for a predetermined amount of time, the cells 14 can then be lysed 28 within or separate from the main bioreactor 22. The cell lysate can then be filtered 30 to remove cell debris. The filtered lysate can be processed so as to separate 32 the protein product from other cellular components, such as other proteins, by well-known separation techniques, such as by chromatography. The protein product can then be purified 34 so as to obtain a substantially pure product or a product having sufficient purity for its intended use. The systems, equipment, and methods of bioprocessing are described in more detail below.

Additionally, bioprocesses can be used to produce extracellular protein products. The bioprocess for preparing an extracellular protein product can be substantially similar to the bioprocess illustrated and described in connection with FIG. 1, but in which the desired product (e.g., protein glycoprotein, or other biological material) is exported from the growing cell into the surrounding media. It will normally not be required or desirable to lyse the cells to recover the biological material. Instead, intact cells are separated from the media (e.g., by centrifugation or filtration) before recovering the desired product from the liquid phase.

Bioprocesses that utilize cells to produce biotherapeutic agents can be effective in producing therapeutic agents that would be prohibitively inefficient to chemically synthesize at the scales required. However, although the efficiency of bioprocessing is much more favorable, it is often compromised by the biology of the cell. Some efficiency losses in bioprocessing result from: the cell producing proteins in response to the gene vector encoding the biotherapeutic agent; the cell producing proteins that are naturally expressed in the cell that have deleterious effects on cell growth; the cell producing proteins that are naturally expressed in the cell that have deleterious effects on the expression of the biotherapeutic agent; the cell producing proteins that are naturally expressed in the cell that inhibit efficient purification of the biotherapeutic agent; the cell over-producing proteins in an amount that interferes with the production of the biotherapeutic agent; the cell producing proteins that associate with the biotherapeutic agent; the cell producing viral proteins that interfere with the production of the biotherapeutic agent; and other processes that interfere with the expression or purification of the biotherapeutic agent. Thus, it is possible to enhance the production of a biotherapeutic agent by inhibiting cellular processes or the production of certain proteins that compromise the preparation of a therapeutic composition having the selected biotherapeutic agent. One method of reducing adverse conditions in cells that compromise the effectiveness of bioprocess in producing biotherapeutic agents can be through the use of siRNA and the RNAi pathway.

RNAi can be achieved artificially within a cell using either synthetic siRNA or siRNA encoded by a vector and inserted into the host cell. In both cases, the polynucleotide is transfected into a cell. While the present invention does not exclude the presence of siRNA encoded by a vector as part of the modified host cell used in the present invention, it may be preferable in certain circumstances to use at least one synthetic siRNA, such as an siRNAdfm, transfected into the host cell or modified host cell as part of the bioprocess (i.e., as a particular aliquot of host cells are grown to produce the bioproduct). When synthetic siRNA is utilized, there is a ramp-up time for the siRNA to be utilized in the RNAi pathway, and at some point the RISC complexes formed from that siRNA is consumed so there is a ramp-down period. The ramp-up period can usually take from 1 to 3 days, and can be characterized by increasing RNAi function until a maximum rate of silencing is incurred. The ramp-down period can fluctuate depending on the amount of siRNA introduced, its chemical modification pattern and the availability of the components in the siRNA pathway, and can be characterized as a decrease in RNAi function until there is essentially no RNAi activity attributable to the synthetic siRNA. As such, the RNAi with synthetic siRNA is transitory.

Additionally, while the present invention is described in connection with biotherapeutic agents, the invention can also be applied to biological materials, biological intermediates or polypeptide intermediates that are utilized in order to prepare a biotherapeutic agent. As such, references herein to a biotherapeutic agent can also refer to biological materials, biologic intermediates, and/or polypeptide intermediates. In part, this is because the same processes that interfere with the production of an endpoint biotherapeutic agent can also interfere with an intermediate product that is then utilized to prepare the biotherapeutic agent. Thus, the present invention can be used to enhance the bioproduction of endpoint biotherapeutics and/or any biological material or polypeptide intermediates that can be used in preparing an endpoint therapeutic agent or used in biological assays.

Also, the present invention can be applied to any biomaterial. A number of biomaterials are prepared by bioprocesses that are not biotherapeutic agents. As such, the present invention can be applied in order to increase the efficiency of the bioprocess that is utilized to prepare the biomaterial. Biomaterials include a wide range of compositions such as lipids, small molecules, enzymes, proteins, protein products, and the like. Accordingly, references herein to biotherapeutic agents should also be construed as being examples of biological materials, and application of siRNA can be used generally for biological materials.

Examples of biological materials that are not biotherapeutic agents that can be produced with increased efficiency by the present invention include any polypeptide that may be utilized in the study of biological function. Examples would include protein over expression for structural analysis by x-ray crystallography, for use in in vitro screening assays for the identification of small molecule drugs, or for the production of important industrial enzymes employed in detergents and certain eye care solutions. Also, the biological material can be biosynthetic silk.

II. RNAi in Bioprocessing

As described, the RNAi pathway can be utilized in order to increase the efficiency of the production of a biological material. In part, increasing the efficiency of producing the biological material can be achieved by modulating various aspects of the bioprocess. This can include: modulating and optimizing various stages of the bioprocess; modulating and optimizing cell lines used in the bioprocess; optimizing the yield of the biological material; automating various stages of the bioprocess; and scaling the bioprocess to industrial-scale processing. Generally, siRNA, as described more fully below, can be used to inhibit the production of polypeptides that adversely affect the ability to obtain a sufficient amount of the biological material at sufficient purity, and thereby optimize the yield of the biological material.

When it is determined that an undesirable protein, such as the types discussed herein, is produced that compromises the production and/or purification of a desired protein, the gene responsible for producing the undesired protein can be identified. The gene may be genomic or a gene vector transfected into the cell. In any event, when the gene encoding the undesirable protein is determined, siRNA can be configured to silence the gene. Various methods are well known in the art for designing siRNA sequences, modifications, and conjugates that target a gene for silencing, such as described below and in the publications and patent application incorporated by reference. The siRNA can then be used to inhibit the production of the undesirable protein, and thereby increase the expression of the desired protein. In some instances, the siRNA can be employed at a specific phase in the cell cycle and/or bioprocess in order to adequately silence the target gene in a manner that increases the efficiency of the production and/or purification of the desired protein. Additional information regarding the use of siRNA and the RNAi pathway in a bioprocess to enhance the production of a desired biological material is described in more detail herein.

Therefore, the present invention provides for the use of siRNA (also referred to as duplex oligonucleotide complex herein) in bioprocesses in order to improve the production and/or purification of the desired biological material, which often a protein product. As such, bioprocesses can be implemented to inhibit the production of selected proteins in protocol where no cloning is needed for such inhibitions. Synthetic siRNAdfm can be added to the host cell for transfection, thereby considerably accelerating the optimization process, and enhancing the ability to externally manage the transience of RNAi. Synthetic siRNAdfm that enhanced delivery into a cell can be advantageous over expressed siRNA because of the ability to precisely control the time point at which the siRNA is introduced and the amount of siRNA.

In certain embodiments, siRNA can be utilized in order to inhibit the production of proteins that may be produced in the cell in response to the gene vector encoding the biological material. When gene vectors are expressed within a cell, proteins other than the desired protein encoded on the gene vector can be produced. In some instances, the production of the desired protein can cause other proteins to be expressed or up-regulated. Cells are complicated systems where changes in the production of one protein, such as a desired protein product, can cause a cascading event that causes the production or over production of another protein. However, the production or overproduction of undesirable proteins produced in response to a desired protein can cause problems in the production and/or purification of the desired protein. Usually, the protein that is produced or overproduced in response to the production of a desired protein is dependent on the specific desired protein and/or cell. Accordingly, comprehensive lists of such proteins that may be produced or overproduced in response to a gene vector may not be readily available; some examples are described herein. In addition, such proteins can be easily identified during the design of a particular bioprocess using a particular recombinant cell line to produce a particular protein-containing product, when a protein is found to interfere with the desired protein. Thus, when the production or overproduction of an undesired protein is found to interfere with the production of a desired protein it can be advantageous to utilize siRNA to inhibit the production of such undesirable proteins.

In one embodiment, siRNA can be utilized in order to inhibit the production or up-regulation of proteins that are expressed in the cell that have deleterious effects on cell growth. Certain proteins are expressed in selected cells that have negative consequences on cell growth. Often such proteins are produced to regulate cell growth. For example, the cell growth-regulating nucleolar protein, encoded by the LYAR gene, can regulate cell growth in a manner that may be insufficient for production of the desired protein product, and thereby inhibit the production of the desired protein product. In some instances, a specific protein or an amount of such a protein can interrupt a cellular process and thereby inhibit cell growth. For example, EBP1 over-expression can inhibit the proliferation of fibroblasts, and thereby inhibit the growth of cells in a bioprocess. In other instances, a specific protein or an amount of such a protein can be toxic to the cell, or can indirectly inhibit cell growth by causing a downstream consequence adverse to the cell. Many different proteins that can be expressed in a cell can be deleterious to cell growth when produced without a corresponding protein that mitigates the adverse effect, or when produced in an amount that causes the adverse effect. Accordingly, proteins that can have deleterious effects on cell growth can be easily identified during the bioprocess when a protein is found to interfere with the desired protein. Examples of proteins that have deleterious effects on cell growth can include the protein products of proto-oncogenes (Liu X, Hu Y, Hao C, Rempel S A, Ye K; PIKE-A is a proto-oncogene promoting cell growth, transformation and invasion. Oncogene; 2007 Jul. 26; 26(34):4918-27. Epub 2007 Feb. 12 and Inoue K, Karashima T, Chikazawa M, Iiyama T, Yoshikawa C, Furihata M, Ohtsuki Y, Shuin T; Overexpression of c-met proto-oncogene associated with chromophilic renal cell carcinoma with papillary growth. Virchows Arch. 1998 December; 433(6):511-5) (e.g., growth factors, kinases, GTPases, and transcription factors), caspases that induce and effect apoptosis, pro-oxidant enzymes that produce oxygen free radicals, ubiquitin ligases that may tag proteins for protolysis, senescence inducing proteins. Thus, it can be advantageous to utilize siRNA to inhibit the production of proteins that directly or indirectly inhibit cell growth.

In one embodiment, RNAi can be utilized in order to inhibit the production of proteins that are expressed at a specific state in a cell cycle or bioprocess that has deleterious effects on cell growth. In some instances, a protein produced at a specific stage in a cell cycle or the bioprocess can inhibit cell growth. While the protein can be advantageous when produced at a proper point in a cell cycle, the production at another point, such as premature production or postproduction can be detrimental to the cell. For example, expression or high level expression of the desired protein product earlier in the bioprocess (e.g., in Phase I and/or Phase II) can be deleterious to cell growth either because of direct effects, indirect effects via the expression of other proteins, or indirect effects because of the extent to which various cellular mechanisms and ingredients (e.g., amino acids) become committed too early to producing the desired protein. Thus, it can be advantageous to utilize siRNA to transiently inhibit premature production of a protein, where premature production of the protein causes adverse effects on cell growth.

In certain embodiments, siRNA can be utilized in order to inhibit the production of proteins that are expressed in the cell so as to cause deleterious effects on the expression of the desired biological material. In some instances, a protein expressed in the cell can have deleterious effects on the expression of the desired biological material. The expression of some deleterious proteins can directly or indirectly reduce the ability of the cell to produce the desired biological material. That can occur from the deleterious protein interacting with the expression pathway of the desired protein by adversely interacting with the gene, mRNA, or protein production machinery of the cell. In some instances the deleterious protein can become associated or bound to the cellular components of the expression pathway, and thereby inhibit production of the desired protein. In other instances, the deleterious protein can degrade the cellular components of the expression pathway. In still other instances, the deleterious protein can degrade or modify the desired protein itself, which compromises the ability to produce the desired protein product. For example, nucleases, endonucleases, exonucleases, DNases, RNases, proteases, glycosylases, kinases, phosphatases, ubiquitinnases, glycosyl transferases, caspases, ATPases, and the like can have deleterious effects on producing the desired biological material. Thus, it can be advantageous to utilize siRNA to inhibit their expression in a bioprocess.

The expression of an undesirable protein that has deleterious effects on the expression of the desired biological material may only be undesirably expressed at a specific phase. That is, an undesirable protein may be advantageously expressed in Phase I, but it is unfavorable when expressed in Phase II and/or Phase III. For example, a protease may be favorably expressed in Phase I, but expression may be unfavorable in Phase II and/or Phase III because expression in Phase I may help cell growth in the later phases, but expression in Phase II and/or Phase III may compromise expression of the desired protein product during these later phases.

In one embodiment, siRNA can be utilized in order to inhibit the production of proteins that are highly-expressed or over-expressed in the cell so as to cause deleterious effects on the expression of the desired biological material. In some instances, high-expression or over-expression of a protein in the cell can have deleterious effects on the expression of the desired biological material, such as a biotherapeutic agent. The high expression of undesired proteins can consume amino acid building blocks that are vital to the production of other proteins (e.g., biotherapeutic agent), and thereby inhibit the production of the desired biological material. Examples of proteins that may be over-expressed can include certain housekeeping genes and proteins involved in cell cycle progression. Additional examples of proteins can be determined empirically on a case-by-case basis. Thus, it can be advantageous to utilize RNAi to inhibit the production of proteins that are over-expressed in the cell so as to compromise the production of the desired biological material.

In one embodiment, siRNA can be utilized in order to inhibit the production of proteins that are expressed in the cell that compromise the ability to purify the desired biological material. In some instances, proteins are expressed in the cell, that inhibit efficient purification of the desired biological material because they have similar physico-chemical characteristics relevant to chromatography (e.g., isoelectric point, hydrophobicity, size, molecular weight, etc.) In other instances the contaminating protein is not similar in physico-chemical characteristics, but contaminates the desired protein because of an affinity for and interaction with the desired protein product. Either mechanism can cause the undesirable proteins to contaminate the desired protein. In this case, in liquid chromatography, the post-column liquid fraction containing the desired protein would also contain the undesirable protein that would become the object of siRNA knockdown. Such proteins would be determined empirically upon analysis of product column fractions. An example of a protein that routinely contaminates chromatographic fractions of desired protein expressed in eukaryotic cells is vimentin, which is difficult to purify from Factor IX. Factor IX is a biotherapeutic agent that is manufactured by a bioprocess. Thus, it can be advantageous to utilize siRNA to inhibit the production of undesirable proteins that tend to interfere with chromatographic purification of desired product. In this way, the purification of the desired protein can be abbreviated or otherwise improved.

In one embodiment, siRNA can be utilized in order to inhibit the production of proteins that are expressed in the cell that post-translationally modify a desired protein product. In some instances, proteins are expressed in the cell during a bioprocess that modify the desired biological material (e.g., biotherapeutic agent), and thereby results in a modified protein that is different from the desired biological material. Glycosylation is one example of post-translational modification of a desired protein product that may result in undesirable glycosylation. Thus, it can be advantageous to utilize siRNA to inhibit the production of proteins that post-translationally modify the desired biological material into a form that is not desirable.

In one embodiment, siRNA can be utilized in order to inhibit the production of proteins that are expressed in the cell that associate, complex, or otherwise bind with the desired biological material. In some instances, proteins are expressed in the cell during a bioprocess that associates with the desired biological material (e.g., biotherapeutic agent), and thereby complicate or prevent purification of the desired biological material. Many proteins form complexes with other proteins, one such example would be the potential interaction of therapeutic monoclonal antibodies that may associate with Fc binding receptors. Accordingly, the formation of such complexes causes problems in attempts to purify a single protein of the complex. Examples of proteins that form complexes include membrane proteins which are prone to aggregation in non-lipid environments, and calcium ion transporters that can increase the intracellular $Ca^{+2}$ concentration and may lead to $Ca^{+2}$ mediated protein cross links. Thus, it can be advantageous to utilize siRNA to inhibit the production of proteins that associate, complex, or otherwise bind with the desired biological material.

In certain embodiments, siRNA can be utilized in order to inhibit the production of viral mRNA and/or proteins in the cell that produces the desired biological material. In some instances, viral mRNA and/or the proteins that are expressed therefrom can be produced in the host cell, that compromise the production of the desired biological material. The expression of deleterious viral genes, such as those encoding nucleases and integrases or other viral proteins, can produce proteins that induce cell death (Rene Daniel et al. Computational Analysis of Retrovirus-Induced scid Cell Death J Virol. 2001 April; 75(7): 3121-3128). Viral mRNA can lead to the expression of such viral proteins. Examples of viral proteins that can inhibit the production of a desired biological material include proteins of similar biophysical properties, aggregation prone viral proteins such as nucleocapsid proteins, senescence inducing proteins and the like. Thus, it can be advantageous to utilize RNAi to inhibit the production of viral mRNA and/or proteins that may be produced by the host cell that inhibit the production of the desired biological material.

In one embodiment, siRNA can be used to inhibit the production of proteins that glycosylate a desired biological material, such as an antibody. Inhibiting glycosylation of certain antibodies can be advantageous for induction of antibody dependent cell-mediated cytotoxicity (ADCC). ADCC is a mechanism of cell-mediated immunity whereby an effector cell of the immune system actively lyses a target cell that has been bound by specific antibodies. The typical ADCC involves activation of natural killer (NK) cells and is dependent on the recognition of antibody-coated cells by Fc receptors [most commonly CD16 (FcγRIII)] on the surface of the NK cell. The Fc receptors recognize the Fc (constant) portion of antibodies such as IgG, which bind to the surface of a target cell. Binding of the Fc region of the antibody to Fc receptors on the NK cells is affected by the glycosylation state of the Fc region of the antibody. In addition, the type of Fc region glycosylation also affects the ability of the antibody to induce ADCC. It has been shown that a reduction in the amount of the carbohydrate fucose present in the N-linked oligosaccharide attached to the Fc region increases the ability of antibodies to induce ADCC. Thus, siRNA can be used to inhibit the production of proteins that glycosylate the Fc region of the antibody.

Targeted immunotherapies employ monoclonal antibodies (MAb) that have been derived to bind to specific ligands that are associated with disease. Antibodies that target soluble factors act to reduce the effective concentration of the secreted factor that is associated with disease progression. Examples of this type of immunotherapy agent would include Humira (Tumor Necrosis Factor α targeting MAb) for rheumatoid arthritis and Avastin (Vascular Endothelial Growth Factor targeting MAb) for colorectal cancer. Another approach is to target a receptor that is expressed on a targeted disease cell and to which some soluble factor may bind to accentuate the disease. In these cases ADCC is one mechanism by which the MAb can actively cause destruction of the disease cells. Examples of this type of immunotherapy agent would include Rituxan (CD20 targeting MAb) for Non-Hodgkins lymphoma and Erbitux (Epidermal Growth Factor Receptor targeting MAb) for colorectal cancer.

The enzyme alpha1,6-fucosyltransferase (alpha1,6-FucT) has been identified as a key mediator of the fucosylation of asparagine lined oligosaccarides in the Fc region of antibodies. In fact the knockout of this gene in Chinese Hamster Ovary cells (CHO) has been shown to increase the ADCC potential of antibodies produced in those cells. SiRNA can be used to transiently inhibit alpha1,6-FucT so that during production of the MAb, the enzyme would not introduce fucose into the N-linked oligosaccharide attached to the Fc region. Thus to optimize the ability of a receptor targeting MAb to induce ADCC one would treat the cells producing the MAb with a siRNA targeting alpha1,6-FucT prior to and/or concurrently with over expression of the recombinant MAb. Thus, siRNA can be used to inhibit the production of alpha1,6-FucT. By contrast, inhibiting the alpha 1,6-FucT using cloned DNA encoding for RNAi may interfere with the growth of the cell line.

Specifically, a novel IgG1 class MAb has been identified that binds with very high affinity to the CD20 receptor (CD20MAb). It is thus an excellent candidate as an immunotherapy for Non-Hodgkins lymphoma that would have superior properties when compared to Rituxan. The desire is to further enhance the ability of CD20MAb to induce ADCC. The gene for the CD20MAb has been stably transfected into HKB11 cells (hybrid of kidney and B cells) and a high efficiency expression clone for the antibody has been isolated (HKB11-CD20MAb). HKB11 cells are a cell line of human origin readily adaptable to serum-free suspension culture under shaking conditions and thus excellent for human therapeutic protein production. The construct for protein over expression is under the control of a heat sensitive promoter such that recombinant protein expression is initiated when the cells are transferred from 37 degrees C. to 28 degrees C. At 28 degrees C. the cells also slow their growth allowing for concentration of cellular energy on MAb over expression. A seed culture of the HKB-11CD20MAb cells are expanded in an innoculant bioreactor under optimal growth conditions at 37 degrees C. The cells produced in the seed bioreactor are then concentrated by centrifugation and brought up to create a "cell slurry" in serum free media containing a modified/conjugated siRNA targeting human alpha1,6-FucT under optimal conditions for passive delivery. Seventy two hours later the resultant innoculant culture is transferred to the main bioreactor for cell expansion at 37 degrees C. Once the cells have reached an optimal density, the temperature is lowered to 28 degrees C. to induce CD20MAb over expression. The CD20MAb protein is then recovered from the media and purified by a series of chromatography, concentration and filtration steps to result in a highly purified preparation of sufficient specification for injection into humans.

In one embodiment, siRNA can be used to inhibit apoptotic factors in order to increase the production yields of the desired biological material. Apoptosis is a process of cell self-destruction and one of the main types of programmed cell death. It involves an orchestrated series of biochemical events leading to a characteristic cell morphology and death. Apoptosis can occur when a cell is damaged beyond repair, infected with a virus, or undergoing stress conditions. Polypeptide over expression is one stress stimuli that may induce apoptosis and thereby limits the population of protein producing cells available during cell culture. Several gene products are involved in apoptosis (e.g. Bcl-2 family, p53, APAF1) and could be targeted by gene silencing to reduce or eliminate apoptosis. One of the key protein classes involved in inducing and effecting apoptosis is the family of cysteine proteases known as caspases. Caspase-9 is an initiator caspase involved in the proteolytic activation of itself and effector caspases (−3, 6, 7, 8, 10) which cascade into a cycle of proteolytic degradation and activation of cellular mechanisms ultimately leading to apoptosis.

Some viruses overcome the induction of apoptosis by taking over the cellular machinery and over produce the biological products (including polypeptides) necessary for their reproduction without the cell employing one of its natural defense mechanisms. For example, baculoviruses encode anti-apoptotic genes that code for cysteine protease inhibitors (p35, the IAP (inhibitors of apoptosis) family, and p49). In fact, the p35 gene product is the most broadly acting caspase inhibitor protein known. Working from this observation, it follows that if one encounters apoptosis of production cell lines during fermentation, one may be able to significantly increase the production yields of the desired polypeptide product by inhibiting one or more caspases using siRNA targeting the caspase encoding mRNA.

A novel anti-inflammatory TNF binding protein, based on the extra-cellular domain of the TNF-R1 (p55) that is fused to the Fc region of IgG1 has shown significant promise as a treatment for rheumatoid arthritis. Because of its superior binding properties to TNFα compared to Enbrel it appears to be an excellent candidate for drug development. Accordingly, a stably transfected HKB-11 cell line (HKB-p55) is created that highly expresses the p55 fusion protein constitutively. When the cell line is first used in small scale cell culture experiments it yields of final product are much lower than anticipated based on the expression observed in the initial research phase. Upon further investigation it is discovered that induction of expression of the p55 fusion lead to a significant level of apoptotic cell death. A small collection of siRNA targeting each of the caspases would be employed, individually and in logical combinations, in experiments on HKB-p55 under stress conditions that simulated those present in the desired cell culture conditions. SiRNA mediated knockdown of caspase-9 is expected to be very effective in reducing the level apoptosis. Furthermore, by adding equimolar concentrations of the siRNA targeting caspase-9 and caspase-6, programmed cell death of HKB-p55 is expected to be further reduced or completely eliminated. In a scale up cell culture, siRNA targeting caspase-9 and 6 could be used together in a serum free media formulation throughout the course of incubating the cell culture to effectively eliminate apoptosis and improved the yield of final product by as much as 10 fold or greater when compared to non-treated cell cultures.

In one embodiment, siRNA can be used to increase the efficiency of the production of specific biological materials in CHO cells. For example, siRNAdfm can be used to inhibit the expression of proteins that compromise the bioprocess for preparing a commercial biological material, such as the biological materials described in Table 1 that are produced in CHO cells. Undesirable protein expression may be determined empirically in each bioprocess. Accordingly, siRNA can be configured to silence the gene that encodes for the undesirable protein, and the siRNA can be utilized in the bioprocess to increase the efficiency of producing or purifying the commercial biological material.

In one embodiment, siRNA sequences can be designed specifically to be less-than-complete in their ability to decrease the expression of the undesirable proteins. In some cases, complete inhibition of certain proteins may reduce cell viability, and therefore have an undesirable overall impact on the yield of protein product. The selection of sequences that partially silence the target gene can be easily prepared using well-known design methods, such as the use of rational design, which is described in more detail herein. Thus, it may be advantageous to use siRNA to only partially inhibit the expression of proteins that compromise the production and/or purification of the desired biological material.

III. SiRNA

Various methods are known for preparing the different forms of siRNA. More particularly, there are 5 commonly known methods for generating siRNAs for gene silencing: (i) chemical synthesis; (ii) in vitro transcription; (iii) digestion of long dsRNA by an RNase III family enzyme (e.g. Dicer, RNase HI); (iv) expression in cells from an siRNA expression plasmid or viral vector; and (v) expression in cells from a PCR-derived siRNA expression cassette. Some of the methods involve in vitro preparation of siRNAs that are then introduced directly into mammalian cells by transfection (e.g., passive, lipofection, electroporation, or other technique). The last two methods rely on the introduction of DNA-based vectors and cassettes that express siRNAs within the cells. All of these methods require careful design of the siRNA to maximize silencing of the target gene while minimizing the effects on off-target genes. However, methods other than chemical synthesis may not allow for precise controllability of the production of the exact desired siRNA. As such, chemi-

TABLE 1

| Product Name | Target/Mechanism of Action | Class of Compound | Product Category | Typical Host Cell | Indication |
|---|---|---|---|---|---|
| Enbrel/Embrel; etanercept | TNF-alpha | Fusion protein of Fc + sol TNF-R | Antibody | CHO | Rheumatoid arthritis; psoriasis etc. |
| Aranesp | EPO-R | Rhu darbepoetin alfa | Protein | CHO | Renal and cancer anemia |
| Rituxan/MabThera; rituximab | CD20 | Rec chimeric mab | Antibody | CHO | $1^{st}$ line treatment of diffuse large B-cell CD20 + NHL plus chemotherapy |
| Procrit/Eprex | EPO-R | Rhu epoetin alfa | Protein | CHO | Renal and cancer anemia |
| Herceptin trastuzumab | HER2 | Rec humanized mab | Antibody | CHO | Metastatic breast cancer |
| Epogen/ESPO | EPO-R | Rhu epoetin alfa | Protein | CHO | Renal and cancer anemia |
| Avastin; bevacizumab | VEGF | Rec humanized mab | Antibody | CHO | Metastatic colorectal cancer |
| Neo-recormon/Epogin | EPO-R | Rhu epoetin beta | Protein | CHO | Renal and cancer anemia |
| Avonex; interferon beta-1a | IFN-R | Rhu interferon β-1a | Protein | CHO | Multiple Sclerosis |
| Rebif; interferon beta-1a | IFN-R | Rhu interferon β-1a | Protein | CHO | Multiple Sclerosis | cal synthesis is a preferred method of siRNA preparation for transient transfection of CHO cells in accordance with the present invention. In part, this is because synthetic siRNA of the present invention can be introduced into a bioprocess at a select time in order to silence a select gene without relying on a cellular system to prepare and/or process the siRNA before being a functional gene silencing entity. Additionally, siRNAdfm having a delivery facilitating moiety can be advantageous allow for passive delivery into cells without use of a polynucleotide carrier.

In one embodiment, a gene silencing composition can include at least a first synthetic siRNA which silences at least a first target gene, wherein the first target gene encodes for an undesirable protein that interferes with a bioprocess that produces a desired biological material, such as a biotherapeutic polypeptide product. The gene silencing composition can be configured such that the siRNA is capable being provided in an amount sufficient for transfecting cells in the bioprocess so as to produce adequate amounts of the desired biological material. This includes synthetic siRNA that has a delivery facilitating moiety for targeting cells for enhanced cellular uptake, such as CHO cells. Also, the siRNA can be rationally designed to target the gene. Furthermore, the gene silencing composition can include a pool of siRNAs.

In one embodiment, the synthetic siRNA in the gene silencing composition can be generated by one of several art-recognized means including chemical synthesis (e.g., 2'-ACE chemistry of U.S. Pat. No. 5,889,136, which is incorporated herein by reference), synthesis using enzymatic procedures (e.g., in vitro Dicer digestion of long dsRNA), or expression from plasmid or vector constructs.

Usually, siRNA are short RNA sequences that include a duplex region that has about 15 to 30 nucleotide base pairs. Preferably, the duplex region is about 17 to about 25 base pairs, more preferably from about 19 to 23 base pairs, and most preferably about 19 base pairs.

In one embodiment, the siRNA is selected to optimize functionality in silencing the target gene. Preferably, the siRNA has between 50% and 100% gene silencing functionality. More preferably the siRNA has a gene silencing functionality between 70% and 100%. Even more preferably, the siRNA has a gene silencing functionality between 80% and 100%. Most preferably, the siRNA has a gene silencing functionality between 90% and 100%. The design of functional genes can be based on providing modifications that increase on-targeting, decrease off-targeting, increase stability, are rationally designed for particular mRNA targets, and combinations thereof.

Additionally, the siRNA antisense strand can have varying levels of complementarity with the target sequence (e.g., mRNA). As such, the sense strand can be substantially homologous with the target sequence. Preferably, the antisense strand can have 50-100% complementarity with the target sequence. More preferably, the antisense strand can have 70-100% complementarity with the target sequence. Even more preferably, the antisense strand can have 80-100% complementarity with the target sequence. Still even more preferably, the antisense strand can have 90-100% complementarity with the target sequence. Most preferably, the antisense strand can have 100% complementarity with the target sequence.

In one embodiment, the siRNA can include at least one mismatch between nucleotides of the sense and antisense strands. Examples include (in the case of a 19 bp duplex) one or more mismatches at nucleotides 6, 14, and/or 18 counting from the 5' end of the sense strand. The mismatch(es) are between the sense and antisense strands but allow substantial complementarity to be retained between the antisense strand and the target mRNA. It should also be noted that in cases where the duplex is longer than 19 base pairs, persons in the art recognize that the position of the modifications and mismatches are altered to ensure that the final (post Dicer processed) molecule has the modification pattern similar to those of the previously described 19 base pair molecule.

Sequences having less than 100% complementarity can have bulges of one or more nucleotides, overhangs, or contain one or more mismatches. In addition, the siRNA can have overhangs of one to six nucleotides associated with the 3' and/or 5' end of the sense or antisense strands. Preferably, the overhang is 2 nucleotides. Additionally, it should be recognized that overhangs can be excluded from the calculation of complementarity, but can have homology or complementarity to the target sequence. Chemical modifications, bulges, or mismatches can direct the RNase-III Dicer to cleave the siRNA or shRNA at a particular position.

A two nucleotide 3' overhang can mimic natural siRNAs and are commonly used, but are not essential. Preferably, the overhangs can include two nucleotides, most preferably dTdT or UU. The siRNA can have two nucleotide overhangs, wherein the hierarchy of C>U>G>A for the internal position and A>G>U>C for the terminal position are preferred. Additional information on siRNA structure and Dicer specificity can be found in Vermeulen A, et. al; The contributions of dsRNA structure to Dicer specificity and efficiency; *RNA* (2005), 11:674-682.

In one embodiment, the siRNA can be configured as a short hairpin siRNA ("shRNA"), which are a form of siRNA that includes a loop structure connecting the sense region with the antisense region to form a hairpin structure. Also, shRNA can have a substantially similar functionality compared to other types of siRNA as described herein. Additionally, an shRNA is not considered a modified siRNA unless the nucleotides include modifications as described in more detail below. In cases in which the siRNA is presented as a hairpin shRNA, the size and orientation of the strands can vary. Preferably, the shRNA, such as synthetic shRNA, present in the gene silencing composition have a sense strand or region and an antisense strand or region. the shRNA can be substantially the same as the siRNA described herein and can include a delivery facilitating moiety conjugated to the siRNA at either end or at any proper position, such as in the loop region.

A. Chemical Modifications

As briefly described, the siRNA in the gene silencing composition can be modified into increase specificity and/or stability. Accordingly, specificity modifications can be incorporated into any siRNA in order to decrease off-targeting. Such specificity modifications can be an aspect of on-targeting. Further descriptions of modifications that enhance stability and/or specificity include those described in PCT patent application number PCT/US04/10343, filed Apr. 1, 2004, PCT application with publication numbers WO 2005/097992 and WO 2008/036825, U.S. provisional patent application Ser. Nos. 60/542,668 and 60/543,661, and U.S. patent application Ser. Nos. 10/551,350, 11/619,993, and 11/857,732, the disclosures of which are incorporated by reference.

Stability enhancing modifications can be especially useful in the present invention because increased stability can increase the duration of siRNA persistence within a cell. As such, stability enhancing modifications can be used to increase the length of time that transient inhibition will occur. Also, the stability enhancing modifications can be used to modulate the ramp-up and/or ramp-down of the RNAi process.

Examples of chemical modifications that can reduce off-target effects include various 2' modifications on the ribose groups of the siRNA, and can also include 5' terminal modifications, which can include a phosphate group. Examples of such chemical modifications can include any combination of the following: 2' modifications on the nucleotides at positions one (i.e., ultimate nucleotide) and two (i.e., penultimate nucleotide) of the 5' end of the sense strand, which are the first 5' sense nucleotide and the second 5' sense nucleotide of the duplex region, respectively; 2' modifications on the nucleotides at position one and/or position two of the antisense strand, which are the first 5' antisense nucleotide and/or the second 5' antisense nucleotide of the duplex region, respectively; and a phosphoryl moiety, such as a phosphate group, on the 5' carbon at the 5' terminal nucleotide of the antisense strand. Also, the modification can replace a 5'-OH group of the sense strand with hydrogen to inhibit kinase phosphorylation. In some instances it can be preferable for the 5' carbon at the sense 5' terminal nucleotide to not have a phosphate group.

In one embodiment, the present invention includes siRNA containing chemical modification patterns designed to enhance the stability of the sense strand, antisense strand, and/or the siRNA duplex. For example, the stabilized siRNA can contain any combination of the following: 2' modifications on the 5' ultimate and penultimate sense nucleotides; 2' modifications on at least one through all pyrimidine sense nucleotides; 2' modifications on the 5' ultimate and/or penultimate antisense nucleotides; 2' modifications on at least one through all pyrimidine antisense nucleotides; and/or a 5' carbon having a phosphate modification at the sense or antisense 5' terminal nucleotide. The 2' modifications can be 2'-O-aliphatic modifications (e.g., 2; -O-methyl) or 2'-halogen modifications. Stability modifications can also include internucleotide modifications with phosphorothioates or methylphosphonates.

In a first example, the siRNA can include a 2'-O-aliphatic modification on the first sense and second sense nucleotides, a 2'-O-aliphatic modification on none or at least one through all of the sense pyrimidine nucleotides, a 2'-halogen modification on at least one through all of the antisense pyrimidine nucleotides, and a 5' carbon phosphoryl modification at the antisense 5' terminal nucleotide. A second example can include a 2'-O-aliphatic modification on the first sense and second sense nucleotides, a 2'-O-aliphatic modification on none or at least one through all of the sense pyrimidine nucleotides, a 2'-halogen modification on at least one through all of the antisense pyrimidine nucleotides, a 5' carbon phosphoryl modification at the antisense 5' terminal nucleotide, and a cholesterol conjugate on the 5' carbon of the first sense nucleotide. A third example can include a 2'-O-aliphatic modification on the first sense and second sense nucleotides, a 2'-O-aliphatic modification on none or at least one through all of the sense pyrimidine nucleotides, a 2'-halogen modification on at least one through all of the antisense pyrimidine nucleotides, a 5' carbon phosphoryl modification at the antisense 5' terminal nucleotide, and a fluorescent tag conjugate on the 5' carbon of the first sense nucleotide, wherein the fluorescent tag can by any well known fluorescent group such as Cy3. A fourth example can include a 2'-O-aliphatic modification on the first sense and second sense nucleotides, a 2'-O-aliphatic modification on none or at least one through all of the sense pyrimidine nucleotides, a 2'-O-aliphatic modification on the first and/or second antisense nucleotides, a 2'-O-aliphatic modification on none or at least one through all of the antisense pyrimidine nucleotides, and a fluorescent tag conjugate on the 5' carbon of the first sense nucleotide. A fifth example can include a 2'-O-aliphatic modification on the first sense and second sense nucleotides, a 2'-O-aliphatic modification on none or at least one through all of the sense pyrimidine nucleotides, a 2'-O-aliphatic modification on the first and/or second antisense nucleotides, a 2'-halogen modification on none or at least one through all of the antisense pyrimidine nucleotides, and a 5' carbon phosphoryl modification at the antisense 5' terminal nucleotide. Additionally, any of the 2'-halogens can be replaced with a phosphorothioate group at the 2' or 3' atom. Also, any of the siRNA can include an overhang at the 3' end of the antisense strand. Optionally, the second antisense nucleotide can comprise a 2'-O-alkyl group such as 2'-O-methyl, and the first antisense nucleotide can comprise a 2'-OH or 2'-O-methyl. In another option, an overhang nucleotide can include a 2' modification.

In accordance with the foregoing, the 2' modifications can be 2'-O-aliphatic modifications. The aliphatic group can include a saturated or unsaturated, substituted or unsubstituted, and branched or unbranched chain having from 1 to 20 carbon or hetero atoms. More preferably, the aliphatic group has less than 10 carbon or hetero atoms, most preferably less than 5 carbon or hetero atoms, or is an alkyl group. In one option, the 2-O-aliphatic modification can be replaced with a 2'-O-aromatic substitution, or include an aromatic group. In another option, the aliphatic group can be cyclic. For example, the 2'-O-alkyl can be selected from the group consisting of 2'-O-methyl, 2'-O-ethyl, 2'-O-propyl, 2'-O-isopropyl, 2'-O-butyl, 2'-O-isobutyl, 2'-O-ethyl-O-methyl (i.e., —CH$_2$CH$_2$OCH$_3$), 2-O-ethyl-OH (i.e., —OCH$_2$CH$_2$OH), 2'-orthoester, 2'-ACE group orthoester, and combinations thereof. Most preferably, the 2'-O-alkyl modification is a 2'-O-methyl moiety. Additionally, when the siRNA includes multiple nucleotides having modifications, there is no requirement that the modification be the same on each of the modified nucleotides. However, as a matter of practicality with respect to synthesizing the molecules of the present invention, it may be desirable to use the same modification throughout the sense strand (e.g., methyl) or the same modification throughout the antisense strand (e.g., fluoro).

Additionally, the 2'-halogen modifications can be selected from the group consisting fluorine, chlorine, bromine, or iodine; however, fluorine is preferred. Similar to the specificity modifications, it may be desirable to use the same 2' modification throughout each respective strand. For example, 2'-O-methyl can be used on the sense strand, and 2'-F can be used on the antisense strand. However, different 2' modifications can be used on different nucleotides within the same strand.

In one embodiment, between about 40% to about 90% of the nucleotides of the sense strand and between about 40% to about 90% of the nucleotides of the antisense strand are chemically modified nucleotides.

In one embodiment, the 19 bp duplex oligonucleotide complex comprises a mismatch between nucleotide 10, 11, 12, 13, or 14 on the antisense strand and the opposite nucleotide on the sense strand, preferably a mismatch between nucleotide 14 on the antisense strand and the opposite nucleotide on the sense strand.

In one embodiment, each chemically modified nucleotide in the duplex oligonucleotide complex is selected from the group consisting of 2' F modified nucleotides and 2'-O-methyl modified nucleotides. Preferably, nucleotides 1 and 2 and all C nucleotides and all U nucleotides on the sense strand are 2' O-methyl modified and all C nucleotides and all U nucleotides on the antisense strand are 2' F modified.

B. Conjugates

In one embodiment of the present invention, the siRNA can include a conjugate coupled to the sense and/or antisense strands. The conjugate can perform a variety of functions or provide additional functionalities to the siRNA. For example, the conjugate can increase the penetration of the siRNA through a cell membrane with or without being complexed with a carrier. Additionally, the conjugates can be labels that can be monitored or identified in order to determine whether or not a labeled siRNA entered a cell.

For example, conjugates can include amino acids, peptides, polypeptides, proteins, antibodies, antigens, toxins, hormones, lipids, cationic lipids, neutral lipids, sphingolipids, nucleotides, nucleosides, polynucleotides, sugars, steroids, carbohydrates, polysaccharides, polyalkylene glycols such as polyethylene glycol and polypropylene glycol, cholesterol, phospholipids, di- and tri-acylglycerols, fatty acids, stearic, oleic, elaidic, linoleic, linoleaidic, linolenic, and myristic acids, aliphatics, enzyme substrates, biotin, digoxigenin, thioethers such as hexyl-S-tritylthiol, thiocholesterol, acyl chains such as dodecandiol or undecyl groups, di-hexadecyl-rac-glycerol, triethylammonium 1,2-di-O-hexadecyl-rac-glycero-3-H-phosphonate, polyamines such as polylysine and polyethylenimine, adamantane acetic acid, palmityl moieties, octadecylamine moieties, hexylaminocarbonyl-oxycholesterol, farnesyl, geranyl geranylgeranyl moieties, fluorescent label moieties such as rhodamines and fluoresciens, radioactive labels, enzymatic labels, and the like. Alternatively, the conjugate moieties can be proteinaceous in nature including peptides that are membrane translocating (e.g. TAT, penetratin, MAP) or cationic (e.g. poly(lys), poly (arg), poly(his), poly (lys/arg/his), or protamine). Preferred conjugates include cholesterol and fluorescent labels.

In one embodiment, the conjugate moiety can be a small molecule that, for instance, targets a particular receptor or (again) is capable of inserting itself into the membrane and being absorbed by endocytic pathways. Thus, small molecules based on adamantanes, polyaromatic hydrocarbons (e.g. napthalenes, phenanthrenes, or pyrenes), macrocycles, steroids, or other chemical scaffolds, are all potential conjugates for the disclosure.

In some cases, the conjugate moieties are ligands for receptors or can associate with molecules that (in turn) associate with receptors. Included in this class are bile acids, small molecule drug ligands, vitamins, aptamers, carbohydrates, peptides (including but not limited to hormones, proteins, protein fragments, antibodies or antibody fragments), viral proteins (e.g. capsids), toxins (e.g. bacterial toxins), and more. Also included are conjugates that are steroidal in nature, such as cholesterol, cholestanol, cholanic acid, stigmasterol, pregnolone, progesterones, corticosterones, aldosterones, testosterones, estradiols, ergosterols, and more, Preferred conjugate moieties of the disclosure are cholesterol, cholestanol, cholanic acid, stigmasterol, and ergosterol. In certain preferred embodiments, the conjugate moiety is cholesterol.

Conjugates, such as cholesterols, can facilitate delivery of the siRNA into a cell. This can include facilitating passive delivery without an additional transfection reagent. Preferably, when the conjugate is a cholesterol, which does not induce cellular toxicity when associated with the siRNA. Accordingly, it is possible for a cholesterol conjugate to eliminate the need for forming a siRNA-carrier complex (e.g., lipoplex). In part, this is because the cholesterol can serve to transport the siRNA across the cell membrane, especially in CHO cells. Coupling cholesterol to the sense strand can alleviate negative effects due to 2' modifications to the sense strand.

Also, cholesterol can associate with one or more proteins or protein complexes in e.g. the blood (e.g. albumin, LDLs, HDLs, IDLs, VLDLs, chylomicron remnants, and chylomicrons) and be delivered to the cell through association with the appropriate receptor for that complex (e.g., the LDLR, low density lipoprotein receptor). The example of delivery via the cholesterol-LDL association is particularly attractive since the opportunity for dozens or hundreds of siRNA to be delivered in a single LDL particle is feasible. For that reason, the inventors can envision packaging cholesterol conjugated siRNAs or siRNA conjugated to derivatives of cholesterol, in one or more natural carriers (e.g. LDLs) in vitro, and using this as an in vivo delivery system.

Additionally, a label, such as a fluorescent conjugate, can be used in order to monitor the delivery of an siRNA into a cell. The fluorescent label can be used in order to photometrically monitor the delivery of the control siRNA into a cell. Preferably, the fluorescent label is a rhodamine or a fluorescien; however, other fluorescent molecules that can be coupled with an siRNA can be used. Specific examples of fluorescent labels include Cy3™, Cy5™ (Amersham), other cyanine derivatives, FITC, one of the ALEXA™ or BODIPY™ dyes (Molecular Probes, Eugene, Oreg.), a dabsyl moiety and the like. It is also possible to use fluorescent microparticles, such as inorganic fluorescent particles as long as the particle has a size that does not affect transfection efficiencies. The labels may be used to visualize the distribution of the labeled siRNA within a transfected cell. In addition, the label can be used to distinguish between transfected cells from non-transfected cells. As such, a population of cells can be transfected with the labeled siRNA and sorted by FACS. Moreover, the fluorescent labels can be particularly well suited for HCS and HTC analytical techniques. For example, cells that have been transfected can be identified, and then be further examined using HCS analysis.

The use of labeled nucleotides is well known to persons of ordinary skill, and labels other than fluorescent labels, such as enzymatic, mass, or radioactive labels, may be used in applications in which such types of labels would be advantageous. Further descriptions of labeled molecules that are applicable for siRNA reverse transfection are found in U.S. Provisional Patent Application No. 60/542,646, 60/543,640, and 60/572, 270 and PCT Application Serial No. PCT/US04/10343, wherein each is incorporated herein by reference.

Labels can be particularly advantageous when cells are transfected outside of the bioreactors (e.g., transfection occurs before Phase I or between Phase I and Phase II). This can allow the use of FACS, HCS and HTC to monitor the cells during the bioprocess.

Additionally, examples illustrating conjugates, uses of conjugates, and methods of making dsRNAs comprising a conjugate are disclosed in the following references: U.S. Provisional patent application Ser. Nos. 60/542,668 and 60/543, 661; U.S. patent application Ser. No. 10/406,908, filed Apr. 2, 2003, published as U.S. Patent Application No. 2004/0198640; U.S. patent application Ser. No. 10/613,077, filed Jul. 1, 2003, published as U.S. Patent Application No. 2004/0266707 A1 on Dec. 30, 2004; and in PCT/US04/10343, international filing date Apr. 1, 2004, published as WO 2004/090105 A2 on Oct. 21, 2004, PCT/US2007/079051, filed Sep. 20, 2007, published as WO 2008/036825 A2 on Mar. 27, 2008, wherein each of the aforementioned applications is incorporated herein by reference. However, an siRNA comprising a conjugate can be synthesized by any suitable method known in the art.

C. Linkers

A conjugate can be attached directly to the siRNA or through a linker. The conjugate can be attached to any sense or antisense nucleotide within the siRNA, but it can be preferably for the coupling to be through the 3' terminal nucleotide and/or 5' terminal nucleotide. An internal conjugate may be attached directly or indirectly through a linker to a nucleotide at a 2' position of the ribose group, or to another suitable position. For example, the conjugate can be coupled to a 5-aminoallyl uridine. The conjugate can be attached to the sense 3' terminal nucleotide, the sense 5' terminal nucleotide, the antisense 3' terminal nucleotide, and/or the antisense 5' terminal nucleotide. In the instance of a delivery facilitating moiety, such as a cholesterol or other sterol derivative, attachment can be preferred at the 3' end of the sense strand. In the instance of a label, such as a dye, attachment can be preferred at the 5' end of the sense strand.

Though not wishing to be limited by definitions or conventions, in this application the length of the linker is described by counting the number atoms that represents the shortest distance between the atom that joins the conjugate moiety to the linker and the oxygen atom of the terminal phosphate moiety associated with the oligonucleotide through which the linker is attached to the oligonucleotide. For example, in embodiments where the conjugate moiety is joined to the linker via a carbamate linkage, the length of the linker is described as the number of atoms that represents the shortest distance between the nitrogen atom of the carbamate linkage and the oxygen atom of the phosphate linkage. In cases where ring structures are present, counting the atoms around the ring that represent the shortest path is preferred. Usually the linkers are about 3 carbon atoms to about 8 carbon atoms in length.

For example, linkers can comprise modified or unmodified nucleotides, nucleosides, polymers, sugars, carbohydrates, polyalkylenes such as polyethylene glycols and polypropylene glycols, polyalcohols, polypropylenes, mixtures of ethylene and propylene glycols, polyalkylamines, polyamines such as polylysine and spermidine, polyesters such as poly (ethyl acrylate), polyphosphodiesters, aliphatics, and alkylenes. An example of a conjugate and its linker is cholesterol-TEG-phosphoramidite, wherein the cholesterol is the conjugate and the tetraethylene glycol ("TEG") and phosphate serve as linkers.

For example, linkers/linker chemistries that are based on ω-amino-1,3-diols, ω-amino-1,2-diols, hydroxyprolinols, ω-amino-alkanols, diethanolamines, ω-hydroxy-1,3-diols, ω-hydroxy-1,2-diols, ω-thio-1,3-diols, ω-thio-1,2-diols, ω-carboxy-1,3-diols, ω-carboxy-1,2-diols, ω-hydroxy-alkanols, ω-thio-alkanols, ω-carboxy-alkanols, functionalized oligoethylene glycols, allyl amine, acrylic acid, allyl alcohol, propargyl amine, propargyl alcohol, and more, can be applied in this context to generate linkers of the appropriate length.

In some embodiments a linker not only provides a site of attachment to the conjugate moiety, but also provides functional sites for attachment to the support and for initiation of oligonucleotide synthesis. Preferably, these sites are hydroxyl groups; most preferably, they are a primary hydroxyl group and a secondary hydroxyl group, to allow them to be chemically distinguished during synthesis of the conjugate-modified solid support. One hydroxyl group, preferably the primary hydroxyl group, is protected with a protecting group that can be removed as the first step in the synthesis of the oligonucleotide, according to methods well understood by those of ordinary skill in the art. Preferably, this protecting group is chromophoric and can be used to estimate the amount of the conjugate moiety attached to the solid support; most preferably, the group is chosen from triphenylmethyl (Tr), monomethoxytriphenylmethyl (MMTr), dimethoxytriphenylmethyl (DMTr) and trimethoxytriphenylmethyl (TMTr). Another hydroxyl group, preferably a secondary hydroxyl group, is derivatized with a functionalized tether that can covalently react with a functional group on the solid synthesis support, according to methods well understood by those of ordinary skill in the art. Preferable tethers are, by way of example, dicarboxylic acids such as succinic, glutaric, terephthalic, oxalic, diglycolic, and hydroquinone-O,O'-diacetic. One of the carboxylic acid functionalities of the tether is reacted with the hydroxyl to provide an ester linkage that is cleavable using basic reagents (hydroxide, carbonate or amines), while the other carboxylic acid functionality is reacted with the synthesis support, usually through formation of an amide bond with an amine functionality on the support.

The linker may also confer other desirable properties on the oligonucleotide conjugate: improved aqueous solubility, optimal distance of separation between the conjugate moiety and the oligonucleotide, flexibility (or lack thereof), specific orientation, branching, and others.

Preferably, the chemical bond between the linker and the conjugate moiety is a carbamate linkage; however, alternative chemistries are also within the scope of the disclosure.

Examples of functional groups on linkers which form a chemical bond with a conjugate moiety include, but are not limited to, hydroxyl, amine, carboxylic acid, carboxylic acid halide, carboxylic acid active ester, carbonyl, chlorocarbonyl, imidazolylcarbonyl, thiol, maleimide, haloalkyl, sulfonyl, allyl and propargyl. Examples of chemical bonds that are formed between a linker and a conjugate include, but are not limited to, those based on carbamates, ethers, esters, amides, disulfides, thioethers, phosphodiesters, phosphorothioates, phosphorodithioate, sulfonamides, sulfonates, sulfones, sulfoxides, ureas, hydrazide, oxime, photolabile linkages, C—C bond forming groups such as Diels-Alder cyclo-addition pairs or ring-closing metathesis pairs, and Michael reaction pairs. In general, the conjugate moiety will have an appropriate functional group either naturally or chemically installed; the linker will then be synthesized with a functional group chosen to efficiently and stably react with the functional group on the conjugate moiety.

Linkers that have the same length, but are capable of associating with two or more conjugates, are also specifically contemplated.

In another embodiment, the linker may be a nucleoside derivative. The nucleoside may be, for example, a ribonucleoside, 2'-deoxyribonucleoside, or 2'-modified-2'-deoxyribonucleoside, such as 2'-O-methyl or 2'-fluoro. The nucleoside may be, for example, an arabinonucleoside or a 2'-modified arabinonucleoside. Using methods well known to those of ordinary skill in the art, purine and pyrimidine nucleosides may be modified at particular sites on the base to provide linkers and functional groups for attachment of conjugate moieties. For example, pyrimidine nucleosides, such as uridine and cytidine, may be modified at the 5-position of the uracil or cytosine base using mercuric acetate, a palladium catalyst, and an allylic reagent such as allylamine, allyl alcohol, or acrylic acid. Alternatively, 5-iodopyrimidines may be modified at the 5-position with a palladium catalyst and a propargylic reagent such as propargyl amine, propargyl alcohol or propargylic acid. Alternatively, uridine may be modified at the 4-position through activation with triazole or a sulfonyl chloride and subsequent reaction with a diamine, amino alcohol or amino acid. Cytidine may be similarly modified at the 4-position by treatment with bisulfate and subsequent reaction with a diamine, amino alcohol or amino acid. Purines may be likewise modified at the 7, 8 or 9 positions using similar types of reaction sequences.

In preferred embodiments, the linker is from about 3 to about 9 atoms in length. Thus, the linker may be 3, 4, 5, 6, 7, 8, or 9 atoms in length. Preferably, the linker is 5, 6, 7, or 8 atoms in length. More preferably, the linker is 5 or 8 atoms in length. Most preferably the linker is a straight chain C5 linker i.e., there are 5 carbon atoms between the atom that joins the conjugate moiety to the linker and the oxygen atom of the terminal phosphate moiety associated with the oligonucleotide through which the linker is attached to the oligonucleotide. Thus, where the conjugate moiety is joined to a C5 linker via a carbamate linkage, there are 5 carbon atoms between the nitrogen atom of the carbamate linkage and the oxygen atom of the phosphate linkage.

D. siRNA with Linked Conjugates

In one aspect, the present disclosure provides a duplex oligonucleotide complex comprising: a sense strand that ranges in size from about 18 to about 30 nucleotides; an antisense strand that ranges in size from about 18 to about 30 nucleotides, wherein the antisense strand has significant levels of complementarity to both the sense strand and a target gene, and wherein the sense strand and the antisense strand form a duplex; a conjugate moiety that facilitates cellular delivery; and a linker molecule that is from about 3 to about 9 atoms in length and attaches the conjugate moiety to the sense strand.

In one embodiment, the conjugate moiety is cholesterol, the linker molecule is 8 atoms in length, and the linker molecule attaches the cholesterol to the 3' end of the sense strand such that the sense strand of the duplex oligonucleotide complex can have Structure 1.

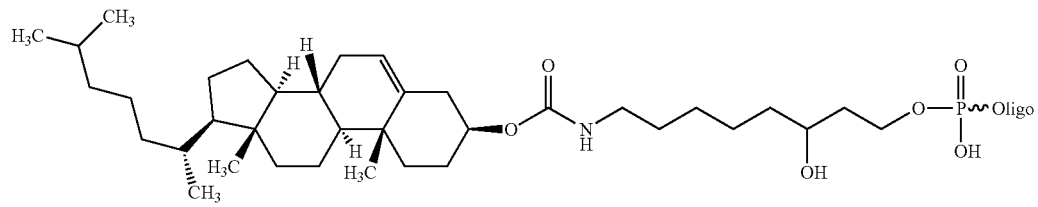

Structure 1

In one embodiment, the conjugate moiety is cholesterol, the linker molecule is 5 atoms in length, and the linker molecule attaches the cholesterol to the 3' end of the sense strand such that the sense strand of the duplex oligonucleotide complex can have Structure 2.

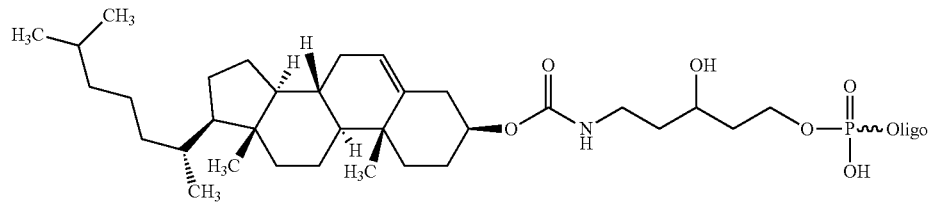

Structure 2

In one embodiment, the conjugate moiety is cholesterol and the linker is a C3 linker attached to the cholesterol via a carbamate group, thus forming a Chol-C3 conjugate-linker. When attached via a phosphodiester linkage to the 5' and/or 3' terminus of a sense and/or antisense oligonucleotide, the resulting conjugate-linker-oligonucleotide can have Structure 3.

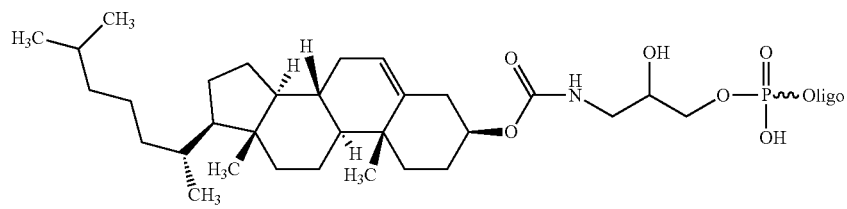

Structure 3

In one embodiment, the conjugate moiety is cholesterol and the linker is a PRO linker (a 4 atom linker) attached to the cholesterol via a carbamate group, thus forming a Chol-PRO conjugate-linker. When attached via a phosphodiester linkage to the 5' and/or 3' terminus of a sense and/or antisense oligonucleotide, the resulting conjugate-linker-oligonucleotide can have Structure 4.

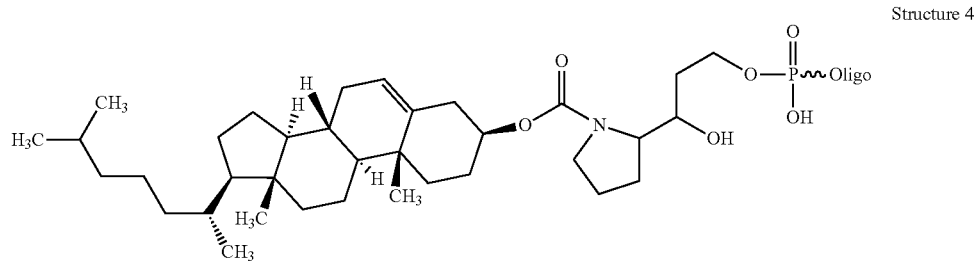

Structure 4

In one embodiment, the conjugate moiety is cholesterol and the linker is a PIP linker (a 6 atom linker) attached to the cholesterol via a carbamate group, thus forming a Chol-PIP conjugate-linker. When attached via a phosphodiester linkage to the 5' and/or 3' terminus of a sense and/or antisense oligonucleotide, the resulting conjugate-linker-oligonucleotide can have Structure 5.

the conjugate/linker embodiments can be utilized with siRNA have any of the modification patterns and/or other features as described herein.

Optionally, the duplex oligonucleotide complex includes a conjugate to facilitate passive delivery into a cell and includes a detectable label, such as a dye molecule or a radiolabel. Such labels are described herein.

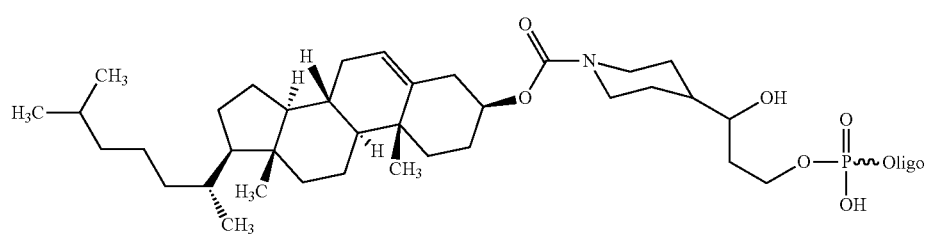

Structure 5

In one embodiment, the conjugate moiety is cholesterol and the linker is a C6-HP (also referred to as "HP6") linker (a 9 atom linker) attached to the cholesterol via a carbamate group, thus forming a Chol-C6-HP conjugate-linker. When attached via a phosphodiester linkage to the 5' and/or 3' terminus of a sense and/or antisense oligonucleotide, the resulting conjugate-linker-oligonucleotide can have Structure 6.

E. Modified siRNA with Conjugates

The siRNA of the present invention can include any combination of chemical modifications, linkers, and/or conjugates as described herein.

In one embodiment, the present invention can include a modified/conjugated siRNA 50 having a sense strand 52 and an antisense strand 54 with sense strand chemical modifica-

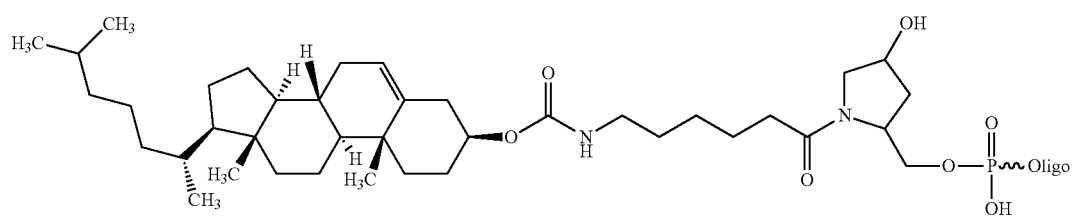

Structure 6

Figure 2:
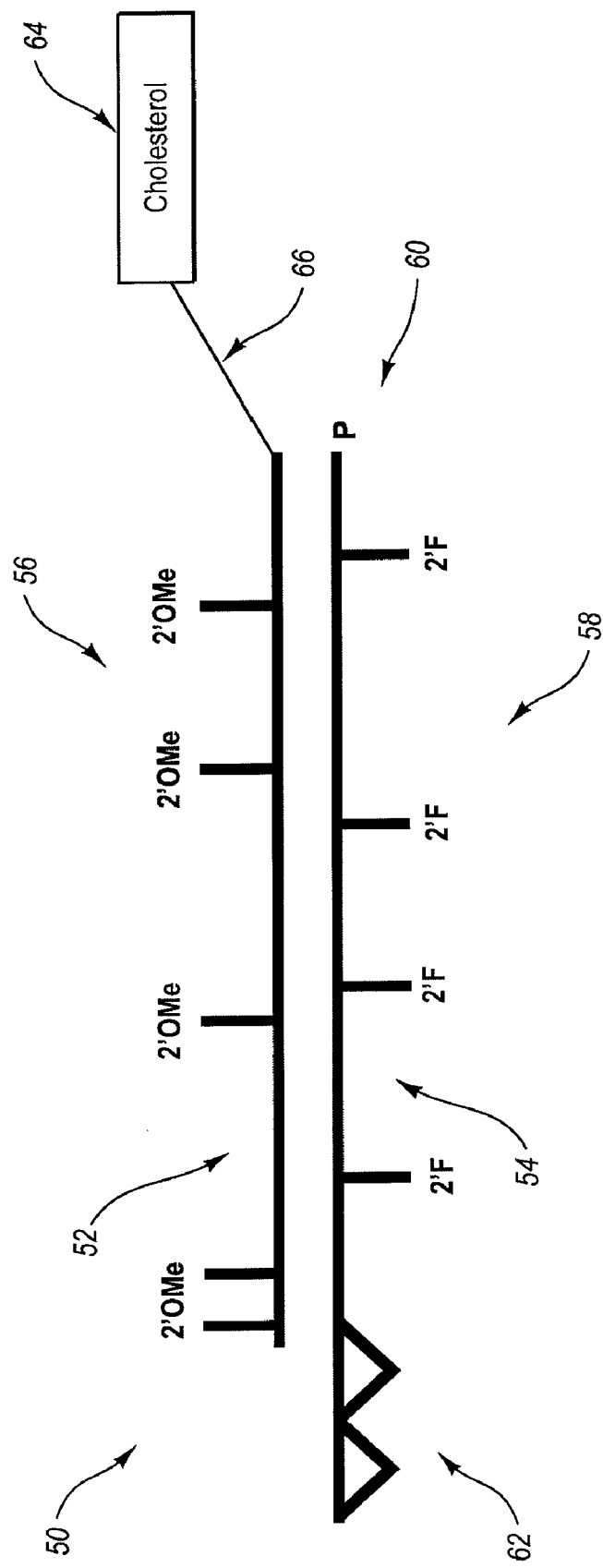
FIG. 2 is a schematic representation of an embodiment of an siRNA having a delivery facilitating moiety.

The C5, C3, C8, PRO, C6-HP, and PIP linkers in the foregoing embodiments can be used with conjugate moieties other than cholesterol, including, for example, cholestanol (CHLN), cholanic acid (CHLA), stigmasterol (STIG), and ergosterol (ERGO). It will also be understood that while the C5, C3, C8, PRO, C6-HP, and PIP linkers exemplified above are shown with a carbamate group attaching the conjugate to the linker, other attachment chemistries may be used. Finally, while the C5, C3, C8, PRO, C6-HP, and PIP linkers in the foregoing embodiments are shown attached to oligonucleotides via a phosphodiester linkage, it will be appreciated that other sites of attachment to oligonucleotides, and other chemistries for attachment to oligonucleotides, may be used. Also, tion patterns 56, antisense chemical modification patterns 58; a 5' phosphate 60, phosphorothioate internucleotide linkages 62, and a conjugate 64 having a C5 linker 66, as shown in FIG. 2. Accordingly, an embodiment of modified/conjugated siRNA can be advantageously used to induce RNAi silencing of genes that encode undesirable proteins, as described herein. A modified/conjugated siRNA can include any of the modification patterns and conjugates with or without linkers as described herein. The modified/conjugated siRNA can be advantageous when used with selected media. Media that has no or low serum can be particularly advantageous because of the benefits of eliminating animal derived products from bioprocesses. Also, the modified/conjugated siRNA can be advantageous in modulating the ramp-up of RNAi by the conjugate facilitating delivery into the cell and to RISC complexes. Also, the modified/conjugated siRNA can induce down regulation 72 hours after addition.

The siRNA molecules useful for the present invention are comprised of a sense strand that ranges in size from about 18 to about 30 nucleotides and an antisense strand that ranges in size from about 18 to about 30 nucleotides. In some embodiments, there is at least one mismatch between a nucleotide on the antisense strand and the opposite nucleotide on the sense strand, preferably a mismatch between nucleotide 10, 11, 12, 13, or 14 on the antisense strand (numbered from the 5' end and not counting any overhang which may be present at the 5' end) and the opposite nucleotide(s) on the sense strand. In certain preferred embodiments, the duplex comprises a single mismatch between nucleotide 14 on the antisense strand (numbered from the 5' end) and the opposite nucleotide on the sense strand. Where the sense and antisense strands are 19 nucleotides in length (not counting any overhangs), position 14 of the antisense strand is opposite position 6 of the sense strand (both numbered from the 5' end of the respective strand, but not counting any overhangs). Where the sense and antisense strands are 18, 20, 21, 22, 23, 24, 25, 26, 27, 28, 29, or 30 nucleotides in length (not counting any overhangs), position 14 of the antisense strand is opposite position 5, 7, 8, 9, 10, 11, 12, 13, 14, 15, 16, or 17 respectively of the sense strand (both numbered from the 5' end of the respective strand, and not counting any overhangs).

One example of a duplex oligonucleotide complex comprises: a sense strand that ranges in size from about 18 to about 30 nucleotides wherein nucleotides 1 and 2 (numbered from the 5' end) are 2'-O-methyl modified and wherein all C nucleotides and U nucleotides are 2'-O-methyl modified; an antisense strand that ranges in size from about 18 to about 30 nucleotides, wherein all C nucleotides and all U nucleotides are 2'-F modified, wherein the antisense strand has significant levels of complementarity to the sense strand as well as a target gene and wherein the sense strand and the antisense strand form a duplex; a 2 nucleotide overhang at the 3' end of the antisense strand comprising phosphorothioate linkages; a cholestanol molecule attached to the 3' end of the sense strand via a C5 linker molecule wherein the cholestanol-linker-sense strand can have Structure 7; a phosphate group at the 5' end of the antisense strand; and optionally, a mismatch between nucleotide 14 on the antisense strand (numbered from the 5' end) and the opposite nucleotide on the sense strand.

Structure 7

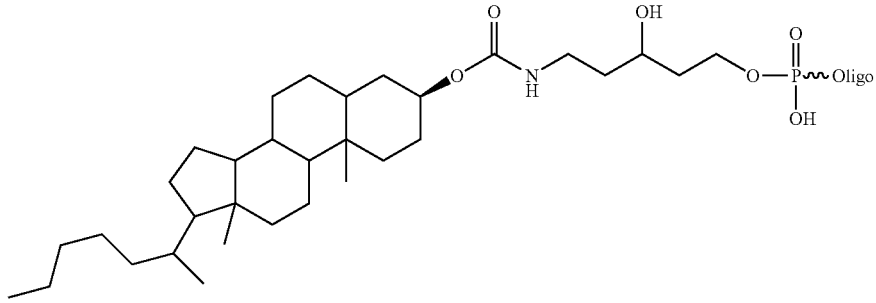

Another example of a duplex oligonucleotide complex comprises: a sense strand that ranges in size from about 18 to about 30 nucleotides wherein nucleotides 1 and 2 (numbered from the 5' end) are 2' O-methyl modified and wherein all C nucleotides and U nucleotides are 2'O-methyl modified; an antisense strand that ranges in size from about 18 to about 30 nucleotides, wherein all C nucleotides and all U nucleotides are 2' F modified, wherein the antisense strand has significant levels of complementarity to the sense strand as well as a target gene and wherein the sense strand and the antisense strand form a duplex; a 2 nucleotide overhang at the 3' end of the antisense strand comprising phosphorothioate linkages; a stigmasterol molecule attached to the 3' end of the sense strand via a C5 linker molecule wherein the stigmasterol-linker-sense strand can have Structure 8: a phosphate group at the 5' end of the antisense strand; and optionally, a mismatch between nucleotide 14 on the antisense strand (numbered from the 5' end) and the opposite nucleotide on the sense strand.

Structure 8

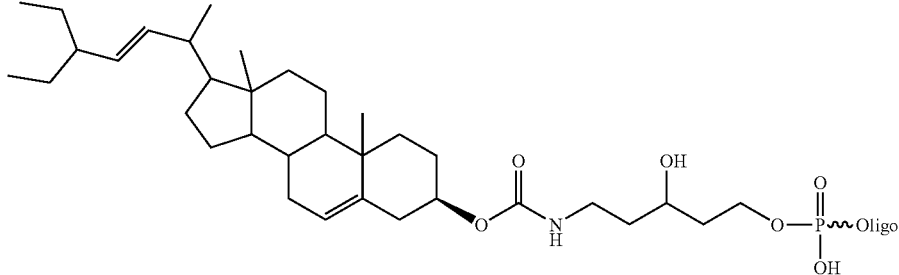

Another example of a duplex oligonucleotide complex comprises: a sense strand that ranges in size from about 18 to about 30 nucleotides wherein nucleotides 1 and 2 (numbered from the 5' end) are 2' O-methyl modified and wherein all C nucleotides and U nucleotides are 2'O-methyl modified; an antisense strand that ranges in size from about 18 to about 30 nucleotides, wherein all C nucleotides and all U nucleotides are 2' F modified, wherein the antisense strand has significant levels of complementarity to the sense strand as well as a target gene and wherein the sense strand and the antisense strand form a duplex; a 2 nucleotide overhang at the 3' end of the antisense strand comprising phosphorothioate linkages; a ergosterol molecule attached to the 3' end of the sense strand via a C5 linker molecule wherein the ergosterol-linker-sense strand can have Structure 9; a phosphate group at the 5' end of the antisense strand; and optionally, a mismatch between nucleotide 14 on the antisense strand (numbered from the 5' end) and the opposite nucleotide on the sense strand.

nucleotides and one through all U nucleotides are 2' F modified, wherein the antisense strand has significant levels of complementarity to the sense strand as well as a target gene and wherein the sense strand and the antisense strand form a duplex; a mismatch at nucleotide 14 (numbered from the 5' end of the antisense strand); a 2 nucleotide overhang at the 3' end of the antisense strand comprising phosphorothioate linkages; a cholesterol molecule attached to the 3' end of the sense strand via a C5 linker molecule; and a phosphate group at the 5' end of the antisense strand.

Structure 9

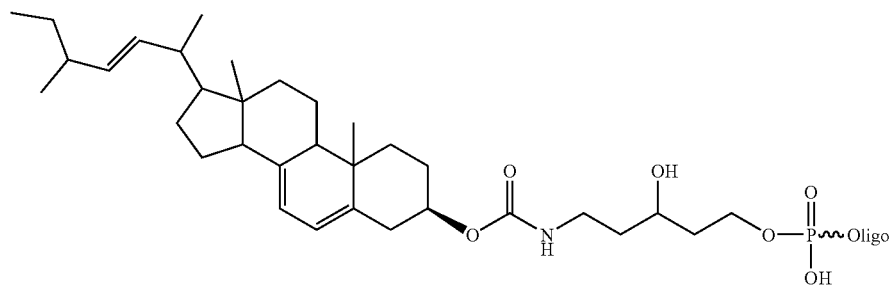

Another example of a duplex oligonucleotide complex comprises: a sense strand that ranges in size from about 18 to about 30 nucleotides wherein nucleotides 1 and 2 (numbered from the 5' end) are 2' O-methyl modified and wherein all C nucleotides and U nucleotides are 2'O-methyl modified; an antisense strand that ranges in size from about 18 to about 30 nucleotides, wherein all C nucleotides and all U nucleotides are 2' F modified, wherein the antisense strand has significant levels of complementarity to the sense strand as well as a target gene and wherein the sense strand and the antisense strand form a duplex; a 2 nucleotide overhang at the 3' end of the antisense strand comprising phosphorothioate linkages; a cholesterol molecule attached to the 3' end of the sense strand via a C5 linker molecule wherein the cholesterol-linker-sense strand can have Structure 2 (above); a phosphate group at the 5' end of the antisense strand; and optionally, a mismatch between nucleotide 14 on the antisense strand (numbered from the 5' end) and the opposite nucleotide on the sense strand.

Additionally, various combinations of the above examples and the modifications and/or conjugates described herein can be utilized for passive delivery into CHO cells.

The modified/conjugated siRNA can have relatively long activity. This can include sustained silencing for up to one week after a single addition. In addition, the modified/conjugated siRNA can be added over multiple courses of treatment allowing for sustained silencing of target genes for many cell doublings.

F. Modified siRNA with Mismatches and Conjugates

The siRNA of the present invention can include any combination of chemical modifications, mismatches, linkers, and/or conjugates as described herein.

An example of a duplex oligonucleotide complex that includes chemical modifications, mismatches, linkers, and/or conjugates is as follows: a sense strand that ranges in size from about 18 to about 30 nucleotides wherein nucleotides 1 and 2 (numbered from the 5' end) are 2'-O-methyl modified and wherein one through all C nucleotides and U nucleotides are 2'-O-methyl modified; an antisense strand that ranges in size from about 18 to about 30 nucleotides, wherein all C In addition to the foregoing example where the duplex is 19 base pairs in length, the mismatch at nucleotide 6 (numbered from the 5' end) of the sense strand can include a 2'-O-methyl modification. For example, when the antisense strand has a C nucleotide that corresponds with nucleotide 6 of the sense strand, the complementary nucleotide is mismatched to be a C nucleotide with a 2'-O-methyl modification instead of a G nucleotide. This forms a mismatch at position 6 on the sense strand. Thus, the sense strand is synthesized to have a mismatch at nucleotide 6 to have the following: a C with a 2'-O-methyl in place of a G; a U with a 2'-O-methyl in place of an A; a G in place of a C; and an A in place of a U.

In view of the foregoing example, the mismatch at nucleotide 6 of the sense strand is preferred. Additionally, in cases where the duplex is 19 base pairs in length, the mismatch can be at nucleotide 14 (numbered from the 5' end) of the sense strand and/or nucleotide 18. The mismatch at nucleotides 14 and/or 18 on the sense strand can be in addition to or instead of the mismatch at nucleotide 6. Thus, the sense strand can have a mismatch at one or any combination of nucleotides 6, 14, and 18.

IV. Reducing Off-Targeting

Off-targeting occurs when an siRNA designed to target and silence one gene unintentionally targets and silences one or more additional genes. Such off-targeting can occur due to varying levels of complementarity between the sense and/or antisense strand of the siRNA and the unintended target mRNA. The consequences that arise from off-targeting can include the silencing of critical genes, and can give rise to a variety of phenotypes (e.g., cell death, cell differentiation). Also, off-targeting can generate false positives in various phenotypic screens. As such, the consequences of off-targeting represent a challenging obstacle to the implementation of large scale, genome-wide siRNA-based phenotypic screens. Accordingly, it is advantageous to reduce and/or eliminate any off-target gene silencing, which can be accomplished by using the modified siRNA of the present invention.

In one embodiment, the consequences of off-targeting can be minimized or inhibited by using pools of siRNAs. Pools of siRNAs have been shown to generate fewer off-target effects as compared to single siRNA. As noted above, the pools may comprise two or more siRNAs that are substantially complementary to different subsequences of one target mRNA or they may be substantially complementary to subsequences of different target mRNAs. For example, a first siRNA and a second siRNA can contain antisense sequences that are substantially complementary to first and second subsequences of one target mRNA. The first and second subsequences can be mutually exclusive or overlapping. The gene silencing composition can include pools that have two, three, four, five, or more different siRNAs. The benefit of reducing off-target effects due to pools of siRNAs is particularly noticeable when at least two siRNA are directed against the same target. Also, pools of modified siRNA, pools of siRNA having hairpin structures, or pools of siRNA having conjugates can be advantageous. The benefits of using pools of siRNA are described in U.S. patent application Ser. No. 10/714,333, filed Nov. 14, 2003, related PCT application PCT/US03/36787, published on Jun. 3, 2004 as WO 2004/045543 A2, U.S. patent application Ser. No. 10/940,892 filed Sep. 14, 2004, published as U.S. Patent Application Publication 2005/0255487 and U.S. Patent Application Publication 2005/0246794 wherein each is incorporated herein by reference.

The reduction of off-targeting or increased specificity can also be achieved by using siRNA concentrations that are below the level that induces off-target effects. As an example, transfection of a single siRNA at 100 nM can induce 90% silencing, yet the high concentration of the siRNA may also induce off-target effects. In contrast, a pool of four siRNAs (e.g., total concentration of 100 nM, 25 nM each) can similarly induce 90% silencing. Since each siRNA is at a four-fold lower concentration, the total number of off-targets is fewer. Thus, in order to obtain silencing with inhibited or no off-target effects, a highly functional siRNA can be used at low concentrations, or pools of siRNA targeting the same gene can be used with each siRNA of the pool having a concentration that is sufficiently low to minimize off-target effects. Preferably, the total amount of siRNAs can be delivered at concentrations that are less than or equal to 100 nM. More preferably, the total amount of siRNAs can be delivered at concentrations that are less than or equal to 50 nM. Even more preferably, the total amount of siRNAs can be delivered at concentrations that are less than or equal to 25 nM. Even more preferably, the total amount of siRNAs can be delivered at concentrations that are less than or equal to 10 nM. Most preferably, the total amount of siRNAs are delivered at concentrations that are less than or equal to 1 nM.

In another embodiment, another way to inhibit or stop off-target effects is to introduce thermodynamic instability into the duplex base pairing at the second antisense nucleotide. For example, this can be achieved through a mismatch between that siRNA antisense nucleotide and the nucleotide located where the complement should be in the target mRNA. Alternatively, an insertion or deletion of a nucleotide in the siRNA antisense strand or sense strand can generate a bulge in the duplex that forms between the siRNA antisense strand or sense strand and the target mRNA or off-targeted sequence. Additionally, thermodynamic instability can also be introduced at the third, fourth, fifth, sixth, and/or seventh antisense nucleotides from the 5' end. However, the resulting thermodynamic instability can lead to silencing of other sequences (i.e., other or secondary off-target effects), but can be avoided by using rationally designed thermodynamic instabilities.

V. Polynucleotide Delivery

The use of RNAi technology in large-scale applications, such as bioprocess manufacturing of protein therapeutics, requires transfection of the siRNA, which is transported from the exterior to the interior of target cells. Commonly, transfection has implemented with polynucleotide carriers, such as lipid carriers. However, polynucleotide carriers can be toxic to cells, and any toxicity may impair the ability of CHO cells to produce a therapeutic. In order to overcome the problems associated with toxicity of polynucleotide carriers, the siRNA of the present invention that include a delivery facilitating moiety conjugated thereto can be passively delivered into cells without the assistance of a polynucleotide carrier. For example, the siRNAdfm (e.g., chol-siRNA as described in the Examples) or siRNA having other targeting moieties can facilitate delivery to and uptake into cells, such as CHO cells, in the bioprocesses described herein.

The mode of transfecting cells with siRNA can modulate the amount of time for ramp-up of the RNAi process to silence the gene encoding the undesirable protein. Also, the mode of transfection can be chosen based on the difficulty of transfecting certain cell lines. It has been found that siRNA that include targeting moieties such as cholesterol and other lipid conjugates, can be delivered passively into CHO cells, which is shown in the Examples described herein. The ability to passively deliver siRNA can be beneficial to the cells because a polynucleotide carrier does not have to be introduced into the cell media. Polynucleotide carriers can be toxic to cells and compromise the health of the cell, and therefore may need to be excluded in some instances. As such, it can be preferred for passive delivery to be used in the bioprocess for preparing the desired biological material. It has been found that siRNA tm (e.g., chol-siRNA) can be passively delivered into CHO cells.

Transfections can be "forward transfections" whereby cells are first seeded and then treated with a nucleic acid or they can be "reverse transfections" (RTF) whereby the nucleic acid is combined with the cells before or during being introduced or seeded into a bioprocess cell culture environment.

VI. Industrial Bioprocessing

Industrial bioprocessing has been used to produce various biological products by culturing living cells that produce the desired biological material. However, the complexity of living systems can create inefficiencies in manufacturing a commercially viable desired biological material. For example, the production of undesirable proteins, such as those described herein, can compromise the ability to efficiently express and/or purify the desired biological material. While a simplified schematic of a bioprocess is provided in FIG. 1, a more detailed schematic of a bioprocess that utilizes the features of the present invention is illustrated and described in connection with FIG. 3.

Figure 3:
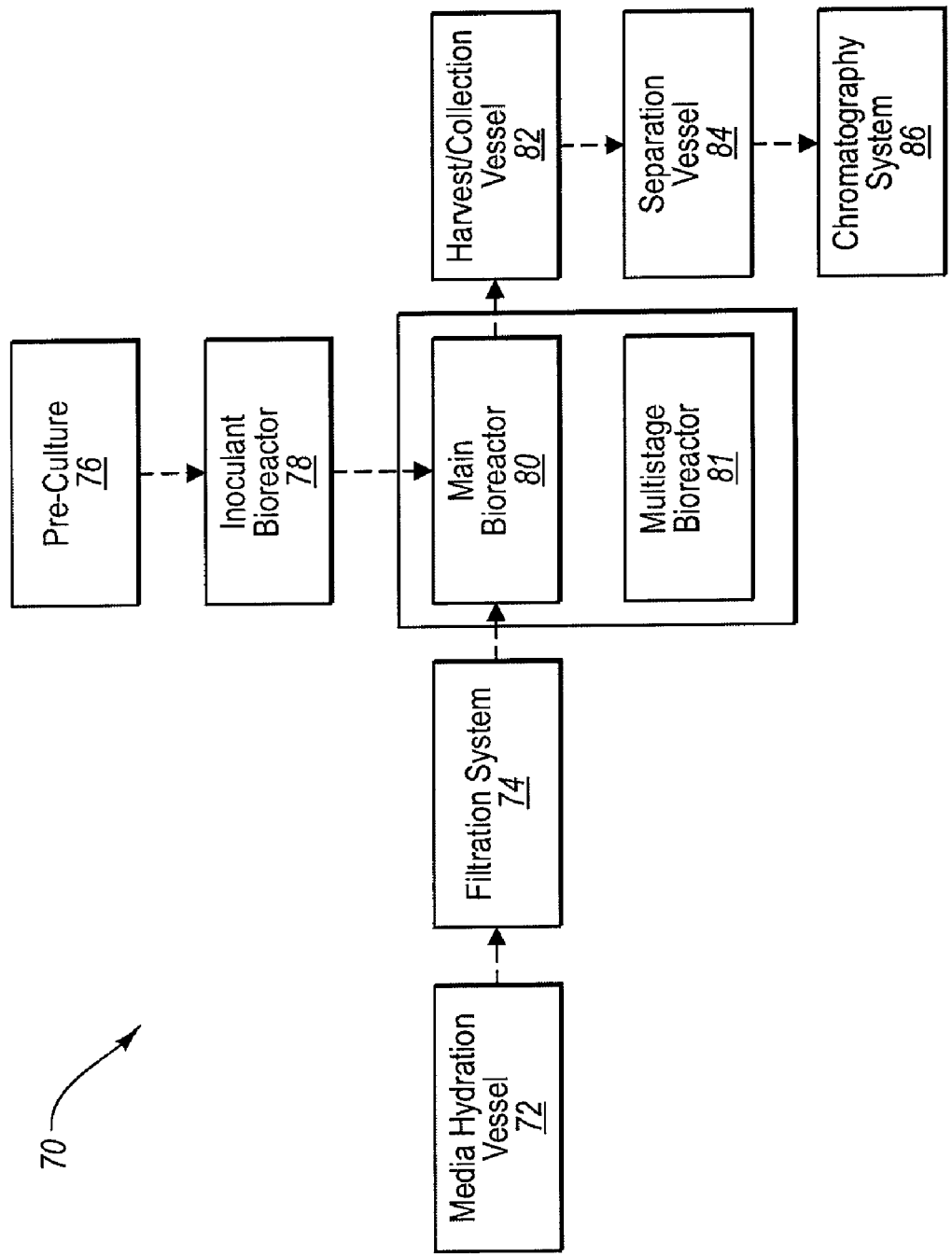
FIG. 3 is a schematic representation of an embodiment of a bioprocessing system.

FIG. 3 provides an illustration of a schematic diagram of a representative bioprocess system 70 in accordance with the present invention. The bioprocess system 70 is shown to include a media hydration vessel 72. Often, bioprocessing materials are provided in powdered form and must be hydrated with purified water prior to use. The hydration process typically comprises combining a precise amount of powdered material and purified water in a closed stainless steel tank (e.g., media hydration vessel 72). Liquid supplements can be added before or after the initial mixing. The hydration and mixing of the materials can occur in the media hydration vessel 72. Once the solution is prepared, the solution is filtered with a filtration system 74 as shown, and may be directly used or dispensed and sealed into sterile containers for shipment or storage.

The bioprocess system 70 can include a pre-culture 76 where the cells that are going to be used in the bioprocess are maintained. The use of RNAi can be implemented within the pre-culture depending on the ramp-up time.

Also, the bioprocess system 70 includes an innoculant bioreactor 78. Innoculant bioreactors 78 are utilized to inoculate the cell culture media with the cell type that is to be used in preparing the biological material. Also, the innoculant bioreactor 78 allows for the cells to grow into a culture that can be utilized in a bioprocess. The time period of initial culturing and growth can be referred to as Phase I.

After a sufficient time for initial growth, the cultured cells can then be cultivated to move into a main bioreactor 80; however, a single reactor can serve as an innoculant 78 and main bioreactor 80. Also, bioprocess systems 70 can include a multistage bioreactor 81. Usually, multistage bioreactors 81 are a series of bioreactors of increasing size. For example, the bioreactors can be arranged as follows: innoculant reactor (Phase I); phase IIA bioreactor; Phase IIB bioreactor; and Phase III bioreactor.

The cell culture media in the often become polluted with cell waste, and the media may need to be replaced prior to being introduced into the main bioreactor 80. As such, the cells can be filtered to remove pollutants from the culture prior to being introduced into the main bioreactor, and new media can be added to the cells.

After the initial growth period and introduction into the main bioreactor 80, the cells can be grown for another time period, which can be referred to as Phase II. During Phase II, the cells are maintained so as to promote optimal growth so that the cells can then be useful for producing the desired protein product. Also, the media provided to the cells in Phase II can be optimized for cell growth by providing the proper nutrients.

At some point the cells move into Phase III where expression of the protein product is favored. Also, Phase III can be based on reaching a maximum cell density, and can be influenced by media changes, new siRNA effects, the phase-out of old siRNA effects, or a combination of such factors. During Phase III, the media can be optimized for the production of the desired protein product. The cells are allowed to produce the desired protein so that an optimal amount of desired protein is produced.

After the protein product is produced by the cells in a sufficient amount or for a predetermined amount of time, the cells are harvested and collected. This can be performed with a harvest/collection vessel 82. However, such harvesting can be conducted within the main bioreactor 80 or the cells can be moved to a harvest/collection vessel 82. When the protein product is a intracellular protein the cells are lysed. When the protein is an extracellular protein, the cell culture media can be collected. After the desired protein product has been exported from the cells into the surrounding media, the media can be separated from intact cells (e.g., by centrifugation or filtration) and the desired proteins (either specifically or with other proteins generally) can be recovered from the media prior to separation (e.g., chromatography).

The cell lysate or collected media can then processed in separation vessel 84 (e.g., filtration or centrifugation) to remove cell debris. The filtration can be achieved by suitable separation techniques that remove debris from the media and desired protein product. Examples of separation techniques include filtration, centrifugation, ultracentrifugation, and the like.

After separating debris from the desired protein product, the resulting composition can be processed by a chromatography system 86 so as to separate the protein product from other cellular components, such as other proteins, by well-known separation techniques. Accordingly, chromatography can be employed so that the desired protein product can then be purified so as to obtain a substantially pure product or a product having sufficient purity for its intended use. FIGS. 4A-4B provide an illustration of a liquid chromatography graph 90 that shows liquid fractions 92. The liquid fraction 92 containing the desired protein product 94 is shown to be contaminated with interfering substances 96 that may need to be silenced with siRNA. As such, siRNA can be employed to inhibit the production of the contaminants. This would produce a liquid fraction 92 that includes the desired protein product 94 and substantially depleted of the interfering substances 96.

In one embodiment, a three stage purification strategy can be employed. The first stage is a capture stage where the goal is to isolate, concentrate, and stabilize the protein product. The second stage is an intermediate purification state where the goal is to remove most of the cellular impurities, such as other proteins, nucleic acids, endotoxins, and viruses. The third stage is a polishing stage where the goal is to achieve high purity by removing any remaining trace impurities or closely related substances, such as proteins that have similar physico-chemical properties. During each of the three phases, certain parameters may need to be optimized for the protein product. Such parameters can include the following: temperature stability; pH stability; organic solvent stability; detergent stability; ionic stability; co-factors for stability or activity; protease stability; sensitivity to metal ions; redox sensitivity; molecular weight; charge potential; biorecogniztion of ligands; and hydrophobicity. Charge-based properties can be used for separation with ion exchange chromatography. Molecular weight properties can be used with size-exclusion chromatography via gel filtration. Hydrophobicity properties can be used with hydrophobic interaction and/or reversed phase chromatography. Biorecognition of ligands can be used with affinity chromatography.

The purified protein product can then be moved to a finishing vessel, where the protein can be formed into a suitable commercial composition. Such a commercial composition can then be moved to bulk storage before being filled into a commercial product container.

In accordance with the present invention, the use of siRNA (e.g., siRNAdfm) can be employed at various stages or phases of the bioprocess. As such, the point where siRNA is introduced to the cells in the bioprocess can be modulated depending on both the nature of the desired protein product and the nature of the undesirable. Accordingly, the introduction of the siRNA to the cells can be controlled in order to optimize the amount of the desired protein that is produced and/or purified.

The factors governing transfection of synthetic siRNA, the RNAi pathway, and/or the bioprocess can be considered in determining the point of the cell cycle and/or bioprocess where RNAi is implemented. The lag between introducing siRNA into the cells and the maxim level of gene silencing (e.g., inhibiting the production of the undesired protein) can be used as a factor in determining the proper point at which RNAi is commenced by introducing siRNA. Also, the duration of effective RNAi can be used as a factor in determining the proper point at which RNAi is commenced by introducing siRNA. For example, the maximum gene silencing potential that can be achieved with siRNA can be meshed with the stage where the undesirable protein is produced in order to determine when RNAi should be implemented. Also, the slowing of RNAi as the RISC complex or other components of the RNAi pathway are consumed can be a factor in determining the stage at which to implement RNAi by introducing siRNA. Thus, the use of siRNA can be integrated within a bioprocess at a stage that allows for the desired effects to be tailored with respect to the function of the cells at that stage.

In one embodiment, it can be advantageous to deliver the synthetic siRNAdfm into the CHO cells in culture during Phase I by passive transfection. In part, the duration of silencing achieved by the siRNAdfm can be utilized as a factor in determining the optimal point for delivery. Some of the factors that can result in siRNAdfm being introduced in Phase I are as follows: the undesired protein is expressed or overexpressed in Phase I; the protein product is expressed or over-expressed in Phase I and the siRNA is configured to inhibit production until a later phase; the duration of gene silencing; the duration of expression and gene silencing of any expressed siRNA in the originally modified host CHO cell; and the like.

In one embodiment, it can be advantageous to introduce the synthetic siRNAdfm to the CHO cells after being collected from the inoculation bioreactor and before being introduced into the main bioreactor. The same factors recited with regard to Phase I can be considered for introducing the siRNAdfm at an intermediate point. In part, the advantage of introducing the siRNAdfm at an intermediate point can be related to the following: concentration of CHO cells; lack of pollutants in the new media; composition of new media is optimal for transfection; new media is serum free; the CHO cells are at a point in the cell cycle where transfection is optimal; and the like.

In one embodiment, it can be advantageous to introduce the synthetic siRNAdfm to the CHO cells during Phase II. The same factors recited with regard to Phase I and the intermediate stage can be considered for introducing the siRNAdfm or vector at Phase II.

In one embodiment, it can be advantageous to introduce the synthetic siRNAdfm to the CHO cells at the outset of Phase III. Since Phase III is the primary stage where it is desirable for the protein product to be produced, the other proteins that are expressed or over-expressed or that interfere with the expression or purification of the desired can be especially problematic. As such, inhibiting the production of undesirable proteins in Phase III can allows for enhance production and/or purification of the desired protein product. Also, the factors recited above may also be applicable to Phase III.

Also, the amount of RISC available for implementing RNAi may be limited by RISC complexes being active in natural RNAi, which can be considered when determining the point at which the siRNA is delivered to the cell. As such, RISC can limit the amount of RNAi that is effectively implemented. In part, this is because the synthetic siRNA, which may be present in large amounts, can be processed into strands which occupy the available RISC complexes. As more of the strands derived from synthetic siRNA occupy the RISC complexes, the RNAi activity of endogenous miRNA of the host cells may be reduced. As the RISC complexes formed with synthetic siRNAs dissipate, there may be room for a new synthetic siRNA to come in and/or the effects of endogenous miRNA may come back.

Additionally, different siRNAs that target different genes for silencing can be applied to the cells at the same time or at different stages. There may be instances where multiple genes can be silenced in order to enhance the production of the desired protein product. This can include multiple genes being silenced at a single stage or over multiple stages.

The desired effects of utilizing siRNA in the present invention can be obtained when only a portion of the cells are transfected. While 100% transfection is preferred, a lesser percentage of cells being transfected can also provide a beneficial effect as described herein. For example, when silencing the target gene and inhibiting the production of the undesired protein during Phases I and II, the cells that are not successfully transfected can immediately begin producing the desired protein product. The cells that are transfected in an early phase with siRNA to inhibit the production of the undesired protein may grow and divide faster in the early phases, and then move into Phase III and increase production of the desired protein product.

Minimal (serum-free) media are commonly used in bioprocessing. The most expensive component of such media is Insulin Growth Factor-1LR3 (IGF-1LR3). Unfortunately, CHO cells (which are frequently used in bioprocessing) secrete IGF-binding protein (IFGBP). This binding protein acts as a reagent sink, effectively reducing the concentration of IGF-1LR3 available to stimulate cell growth. Accordingly, siRNA (high, medium, and/or low potency) that target IGFBP can be used to improve the amount of IGF-1LR3 for cell growth. The siRNA could be added to CHO cells prior to Phase I to reduce the effective concentration of IGFBP, thus reducing the amount of IGF-1LR3 needed to stimulate cell growth.

In one embodiment, bioprocessing can be used in a method for producing a protein-containing product. Such a method can include: culturing a recombinant host cell containing nucleic acid encoding at least a portion of the protein-containing product; contacting the recombinant host cell with a synthetic siRNA under conditions in which the synthetic siRNA transfects the recombinant host cell and inhibits the expression of a first protein, wherein undesirable expression of the first protein decreases the production of the protein-containing product; incubating the recombinant host cell with the synthetic siRNA under conditions that allow cell replication and expression of the protein-containing product; and recovering the protein-containing product. The bioprocessing method can also include the following: culturing a host cell; infecting the host cell with a viral construct containing nucleic acid encoding at least a portion of the protein containing product; incubating the host cell either before or after the infecting step, or both, with a synthetic siRNA under conditions in which the synthetic siRNA transfects the host cell and inhibits the expression of a first protein, wherein undesirable expression of the first protein decreases the production of the protein-containing product; and recovering the protein-containing product.

The bioprocessing method can also include: inhibiting expression of the first protein during a first portion of the step of incubating the recombinant host cell while the recombinant host cell is replicating; and expressing the protein-containing product during a second portion of incubating the recombinant host cell after the expression of the first protein has been inhibited.

The bioprocessing method can include providing the siRNA, such as any siRNA described herein, to the bioprocessing system in a manner in accordance with at least one of the following: the synthetic siRNA contacts the recombinant host cell prior to incubating the recombinant host cell in a bioreactor; the recombinant host cell is incubated for a first time period in a bioreactor, is then contacted with the synthetic siRNA, and is then incubated for a second time period in a bioreactor; incubating the recombinant host cell for a first time period in a bioreactor in the absence of the synthetic siRNA, contacting with the synthetic siRNA in a bioreactor, and incubating the recombinant host cell for a second time period in a bioreactor.

Additionally, the bioprocessing method can be performed in order to inhibit the production of the first protein so as to enhance bioproduction of the protein-containing product compared to instances wherein production of the first protein is not inhibited. Also, the method can include at least one of the following: inhibiting production of fucosyl transferase; inhibiting production of caspases to inhibit apoptosis; silencing cell cycle progression genes to inhibit cell proliferation; silencing pro-senescence genes to inhibit host cell death; silencing calcium transporter genes to limit cross links; silencing a gene encoding CD16(Fc)(RIII) to prohibit aggregation; silencing genes encoding factors that destabilize transcriptions and/or affect translation; or silencing genes encoding factors associated with glycosylation of proteins.

Also, the bioprocessing method can include: infecting the recombinant host cell with a viral construct containing nucleic acid encoding at least a portion of the protein containing product; and incubating the recombinant host cell before and/or after being infected with the viral construct with the synthetic siRNA under conditions in which the synthetic siRNA transfects the host cell and inhibits the expression of a first protein.

A. Bioprocesses Including, Viral Infection

The advantages of the present invention, using siRNA to suppress a targeted gene and its protein, are also applicable to bioprocesses in which a host cell is infected during the process with a virus. Such bioprocesses include the use of the baculovirus expression system in which insect-derived host cells are replicated before being infected with baculoviral constructs containing nucleic acid sequences coding for the polypeptide portion of a glycoprotein bioproduct. Also, the baculovirus expression system can be used for the production of vaccines by infecting cultured mammalian host cells with modified viral particles. For these processes, the common phases are: Phase I—growth and division of the host cells from an innoculant aliquot in a small bioreactors or vessel; Phase IIA—further growth of the host cells in a larger bioreactor; Phase IIB—infection of the host cells with baculoviral construct or viral particle; Phase IIC—concurrent cell growth, division and infection of all or a majority of the host cells in the bioreactor; Phase III—final production of viral-coded proteins and cell lysis.

According to the present invention, siRNA can be used to suppress: before or during Phases I and IIA, protein gene products that restrict cell growth and division; before or during phases IIA, IIB or IIC, protein gene products that inhibit viral infection; before or during phases IIB, IIC and III, protein gene products that interfere with the production and stability of the desired viral gene products (including that of the nucleic acid strand inserted into baculovirus); before or during phases IIC or III proteins that may interfere with the separation (e.g., via liquid chromatography) of the desired bioproduct, especially from a baculovirus insert.

VI. Host Cells and Media

Bioprocesses can be conducted with many different cell types. This includes a variety of types of eukaryotic cells as host cells. The host cell type is usually selected based on the desired biological material or the reagents that are utilized. Accordingly, it is contemplated that essentially any and all eukaryotic cell types may be inappropriate for producing some specific biological material. Accordingly, various types of host cells can be used depending on specific needs.

In one embodiment, the present invention may be used in connection with a diverse type of eukaryotic host cells from a diverse set of species of the plant and animal kingdoms. Preferably, the host cells are from mammalian species including cells from humans, other primates, horses, pigs, and mice. For example, cells can be PER.C6 cells, HT-29 cells, LNCaP-FGC cells A549 cells, MDA-MB453 cells, HepG2 cells, THP-1 cells, miMCD-3 cells, HEK 293 cells, HeLaS3 cells, MCF7 cells, Cos-7 cells, CHO cells and CHO derivatives, CHO-K1 cells, BxPC-3 cells, DU145 cells, Jurkat cells, PC-3 cells, Capan-1 cells, HuVEC cells, HuASMC cells, HKB-11 human differentiated stem cells such as osteoblasts and adipocytes from hMSC; human adherent cells such as SH-SY5Y, IMR32, LAN5, HeLa, MCF10A, 293T, and SK-BR3; primary cells such as HUVEC, HUASMC, and hMSC; and other species such as 3T3 NIH, 3T3 L1, ES-D3, C2C12, H9c2 and the like. Additionally, any species of plant may be used to determine an effect of gene silencing. Since CHO cells are used in preparing a significant number of biotherapeutic agents, as shown in Table 1, it is preferable that the siRNA of the present invention be capable of entering CHO cells. The experiments described below show an siRNAdfm having a cholesterol coupled to the siRNA via a linker are effective in passive delivery into CHO cells.

Additionally, during the transfection phase of the bioprocess, it can be advantageous to utilize a media that has low serum content or is free of serum. Many types of media are prepared normally and as having low serum content and/or being free of serum. Low serum media or serum-free media can be prepared by simply not affirmatively introducing serum (e.g., fetal bovine serum) into the media. Also, a serum-containing media can be processed through a cholesterol containing filter/column in order to remove a significant amount or all of the serum components that can interact with cholesterol. It is advantageous to use low serum or serum-free media during transfection because the serum components (e.g., albumin) may adversely interact with the siRNA, especially Chol-siRNA, and reduce the efficacy of the siRNA to be delivered into the cells. The low serum or serum-free media can be provided to the cells prior to the transfection phase in any appropriate manner for replacing cell media. For example, the cells can be withdrawn from any large bioprocessing vessel and placed in low serum or serum-free media with the siRNAdfm. Once a sufficient amount of time or incubation of the cells with the siRNAdfm has occurred, lipids can be added to the cell culture or the cells can be reintroduced into the larger vessel with media having a higher or normal serum content. Additionally, the in vitro medium can be a low serum or serum-free medium.

For example, siRNAdfm, (e.g., chol-siRNA) can be utilized in a transfection phase of the bioprocess in a medium that has less than 3% serum or no serum. The low serum or serum-free media can be advantageous for siRNAdfm that have a cholesterol conjugate because such media has reduced chance of cholesterol binding substances (e.g. albumin) adversely binding with the siRNAdfm.

Also, the growth mode can be a factor in determining host cell type. In some instances, it can be preferable for the cells to be adherent cells that attach and propagate on a surface of the bioreactor. This can include any surface that is in contact with the media. In other instances, it can be preferable for the cells to be grown on particles that are suspended in the media. Cells on suspension particles can provide unique benefits as well as obstacles. In another instance, it can be preferable for the cells to be suspension cells.

Additionally, industrial level bioprocesses may require very large cell numbers, and bioproduction facilities range from 1 liter to 10,000 liter bioreactors. The ability to culture cells in suspension reduces the physical space required to produce biological materials. As such, suspension cultures can provide advantages in bioproduction by needing less bioreactor surface area compared to adherent cells.

VII. Bioreactors

Bioprocesses according to the present invention can be conducted with each incubation step performed on one of many different bioreactors of various types known in the art. The bioreactors are configured to be suitable for culturing cells, and the selection of bioreactor for a particular phase or step can be based on various parameters described herein, such as the desired biological material, cell type, and the like. Examples of suitable bioreactors that can be utilized include cell factories, roller bottles, spinner flasks, stacked flasks, rocker-type bioreactors, stirred tank bioreactors, vapor-lift bioreactors, and the like. Thus, essentially any bioreactor or cell culture container that is suitable for growing eukaryotic cells in medium or large volumes can be employed in one or more phases in the present invention.

Other containers commonly used in a bioprocess for culturing eukaryotic cells are known as stacked flasks. Descriptions of stacked flasks can be found in U.S. Pat. Nos. 5,310,676, 6,569,675, and 6,818,438. Stacked flasks are available in various formats, and can be used with adherent cells, cells on suspension particles, and suspension cells. An exemplary stacked tray type bioreactor is the Nunc Cell Factory, which is described in U.S. Patent Application Publication No. 2007/0065933, WO 04/076609, EP 1599571A, and PCT/DK04/00127. However, other stacked tray type bioreactors can be used and are well known in the art. Bioreactors of this type would most commonly be used in Phase I of the bioprocess and are more likely to be used for adherent cells grown on a bioreactor surface (rather than in suspension).

One type of container commonly used in a bioprocess for culturing cells is known as a roller bottle. Roller bottles are generally cylindrical, and are adapted to rotate about their vertical axes. The internal surfaces of such roller bottles provide active regions for culturing cells. A liquid growth medium is introduced into the roller bottle, and the rotating movement of the bottle keeps the internal surfaces wetted with the liquid medium, thereby encouraging the growth of cells. Rotating rollers of an appropriate apparatus rotate these roller bottles. Various approaches have been used to increase the internal surface area of roller bottles. One approach has been to increase the amount of actual surface area available for cell growth. Also, roller bottles are suited for suspension cells and the innoculant bioreactor or Phase I bioreactor, because roller bottles are generally limited to 4 liters each.

Another type of container commonly used in a bioprocess for culturing eukaryotic cells is known as a spinner flask. Spinner flasks work via placement on a magnetic stirring instrument, and are designed for use with suspension cells, or with anchorage dependent cells attached to microparticles. Again, because of size limitations, spinner flasks are most likely to be used in the innoculant bioreactor or Phase I bioreactor.

Rocker-type bioreactors such as those sold by Wave Biotech Inc. of Sommerville, N.J. can be used in the present invention, especially in the innoculant bioreactor or Phase I bioreactor. Because such devices rock a polymeric bag containing a liquid phase and a vapor phase, they have special applicability to suspension cells and to adherent cells attached to suspended particles. Among the particles that are suitable for this application are HyQSphere microcarriers from HyClone Laboratories of Logan, Utah and MicroHex microcarriers from Nunc A/S of Rosskilde, Denmark. Additional information regarding microparticles (e.g., cell microcarriers) that can be suspended in media can be found in U.S. Pat. No. 6,214,618).

Stirred tank bioreactors can be especially advantageous in any of the Phases of the present invention and especially Phases II and III. Stirred tank bioreactors in steel vessels are well known to be used in bioprocesses. Examples of stirred tank bioreactors with a single-use polymeric chamber or liner can be found in U.S. Application Publications 2006/0280028 and 2006/0270036 and PCT publications WO 06/116139, WO 06/1161069, WO 06/116067, WO 05/104706, and WO 05/104706.

It is preferred to conduct two or more of the phases of the present method in bioreactors having a polymer contact surface, such as the treated polystyrene surfaces of certain of the Nunc products described above or the polyolefin surface layers of the HyQ bioprocess containers (from HyClone Laboratories of Logan, Utah) applicable to the above rocker-type and stirred tank bioreactors described above. Such bioreactor surfaces, and the surfaces of any microcarriers used with adherent cells, should be selected for compatibility with the cells, media and other ingredients used and with the purity requirements desired for the ultimate bioproduct. Thus, for some therapeutic bioproducts, it is preferred that all contact surfaces be animal derived component free.

Additionally, the bioreactors used in the present invention can be configured to be batch or continuous reactors depending on the requirements of the bioprocess overall of for the particular Phase. Batch and continuous bioprocesses are commonly employed for producing biological materials, and the equipment, including the bioreactors of each type described above, are well known in the art.

Additionally, the bioreactors used in the present invention can be configured, attached or equipped to receive doses or feeds of siRNA solutions in a sterile and controllable manner.

This disclosure recites a number of references, and each reference recited herein is specifically incorporated herein by specific reference in its entirety.

EXAMPLES

The following Examples were performed with siRNA having the sequences as shown in Table 2 and Table 3. The siRNA in Tables 2 and 3 have been prepared to include: 2'-O-methyl modifications on the 5' ultimate and penultimate sense nucleotides and on all C and U sense nucleotides; 2'F modifications on all C and U antisense nucleotides; a two nucleotide antisense overhang being a UU that are phosphothioate linked (these UU are not 2'-O methylated nor 2'F); a C5 linker on the 3' terminus of the sense strand; and a cholesterol conjugate on the distal terminus of the linker.

TABLE 2

| Gene Name | Accession Number | siRNA | siRNA sequence (AS), 5'->3' |
|---|---|---|---|
| TP53 | U50395 | SEQ ID NO: 1 | UGACCUCGGAUCUUAAGGGUU |
|  |  | SEQ ID NO: 2 | AGCUCUUGAAACAUCUUGAUU |
| CASP3 | AY479976 | SEQ ID NO: 3 | UAUUCCUUCUUCACCAUGGUU |
|  |  | SEQ ID NO: 4 | UACUGUUUCAGCAUGGCACUU |
|  |  | SEQ ID NO: 5 | UUAUUAUUAACUAUUAUACUU |
|  |  | SEQ ID NO: 6 | AUAAAUUCAAGCUUGUCGGUU |

TABLE 2-continued

| Gene Name | Accession Number | siRNA | siRNA sequence (AS), 5'->3' |
|---|---|---|---|
| Bak | AY479976 | SEQ ID NO: 7<br>SEQ ID NO: 8<br>SEQ ID NO: 9<br>SEQ ID NO: 10 | GGUCUCUUGUUCCUGAUGGUU<br>AGCAAAUUGUCCAUCUCGGUU<br>UCUUAAAUAGGCUGGAGGCUU<br>GAAAACAUAGCUUCGAAAGUU |
| Bax | EF104643 | SEQ ID NO: 11<br>SEQ ID NO: 12<br>SEQ ID NO: 13<br>SEQ ID NO: 14 | UAGCAAAGUAGAAAAGGGCUU<br>UGUUCUUCCAGAUCGUGAGUU<br>UCAACUUCUUGGUAGACGGUU<br>UCCACAUUAGCAAUCAUCCUU |
| NTC | Non-Target Control | SEQ ID NO: 15<br>SEQ ID NO: 16<br>SEQ ID NO: 17<br>SEQ ID NO: 18 | UGGUUUACAUGUCGACUAAUU<br>UGGUUUACAUGUUUUCUGAUU<br>UGGUUUACAUGUUUUCCUAUU<br>UGGUUUACAUGUUGUGUGAUU |

TABLE 3

| Gene Name | Accession Number | siRNA | Sense strand siRNA sequence (S) 5'->3' |
|---|---|---|---|
| TP53 | U50395 | SEQ ID NO: 19<br>SEQ ID NO: 20 | CCCUUuAGAUCCGAGGUCA<br>UCAAGuUGUUUCAAGAGCU |
| CASP3 | AY479976 | SEQ ID NO: 21<br>SEQ ID NO: 22<br>SEQ ID NO: 23<br>SEQ ID NO: 24 | CCAUGcUGAAGAAGGAAUA<br>GUGCCuUGCUGAAACAGUA<br>GUAUAuUAGUUAAUAAUAA<br>CCGACuAGCUUGAAUUUAU |
| NTC | Non-Target Control | SEQ ID NO: 25<br>SEQ ID NO: 26<br>SEQ ID NO: 27<br>SEQ ID NO: 28 | UUAGUgGACAUGUAAACCA<br>UCAGAuAACAUGUAAACCA<br>UAGGAuAACAUGUAAACCA<br>UCACAgAACAUGUAAACCA |

(Bold in lower case indicates the mismatched nucleotides)

Example 1

The ability of siRNA having a cholesterol moiety (i.e., chol-siRNA) linked thereto for delivery into CHO cells was examined. CHO cells are one of the most common cell types used in bioproduction of therapeutic agents, and are used as a model system with respect to bioprocessing. To test the applicability of chol-siRNA technology in this model system, two chol-siRNAs for silencing TP53, a tumor suppressor gene, were synthesized. The first chol-siRNA (i.e., chol-siRNA #1) had an antisense sequence of 5'-UGACCUCGGAUCU-UAAGGGUU (SEQ ID NO: 1), and the second chol-siRNA (i.e., chol-siRNA #2) had an antisense sequence of 5'-AGCU-CUUGAAACAUCUUGAUU SEQ ID NO: 2). The siRNA included a mismatch at nucleotide 6 counting from the 5' end of the sense strand, as shown in Table 3.

The chol-siRNA used in these experiments contained the following attributes: 1) 19 bp core double strand riboligo-nucleotides; 2) sense strand modifications consisting of 2'-O-methyl modifications on nucleotides 1 and 2 (counting from the 5' end of the strand), 2'-O-methyl modifications on all C and U nucleotides (i.e., pyrimidine nucleotides); a C5 linker on the 3' terminus of the sense strand; a cholesterol conjugate on the distal terminus of the linker; and 3) antisense strand modifications including 2' F on all C and U nucleotides (i.e., pyrimidine nucleotides); a 5' phosphate on the 5' terminus of the antisense strand; a 2 nucleotide 3' overhang containing phosphorothioate internucleotide linkages. (see FIG. 2). A suspension CHO cell line (CHO 1-15) was used for these studies.

Cells were first plated (2.5-20 K cells per well in a 96 well plate) and eighteen to twenty-four hours later, the media was changed to one of two serum-free media (CDM4 CHO media, or Reduced Serum (RS) media, HyClone) containing either of the two different chol-siRNAs targeting p53 for silencing (0.125-1.0 micromolar chol-siRNA). Cells were then incubated for an additional 48-72 hours before the levels of gene knockdown were assessed using branched DNA technology (Panomics). All data were performed in triplicate and GAPDH expression was used for data normalization.

Figure 5B:
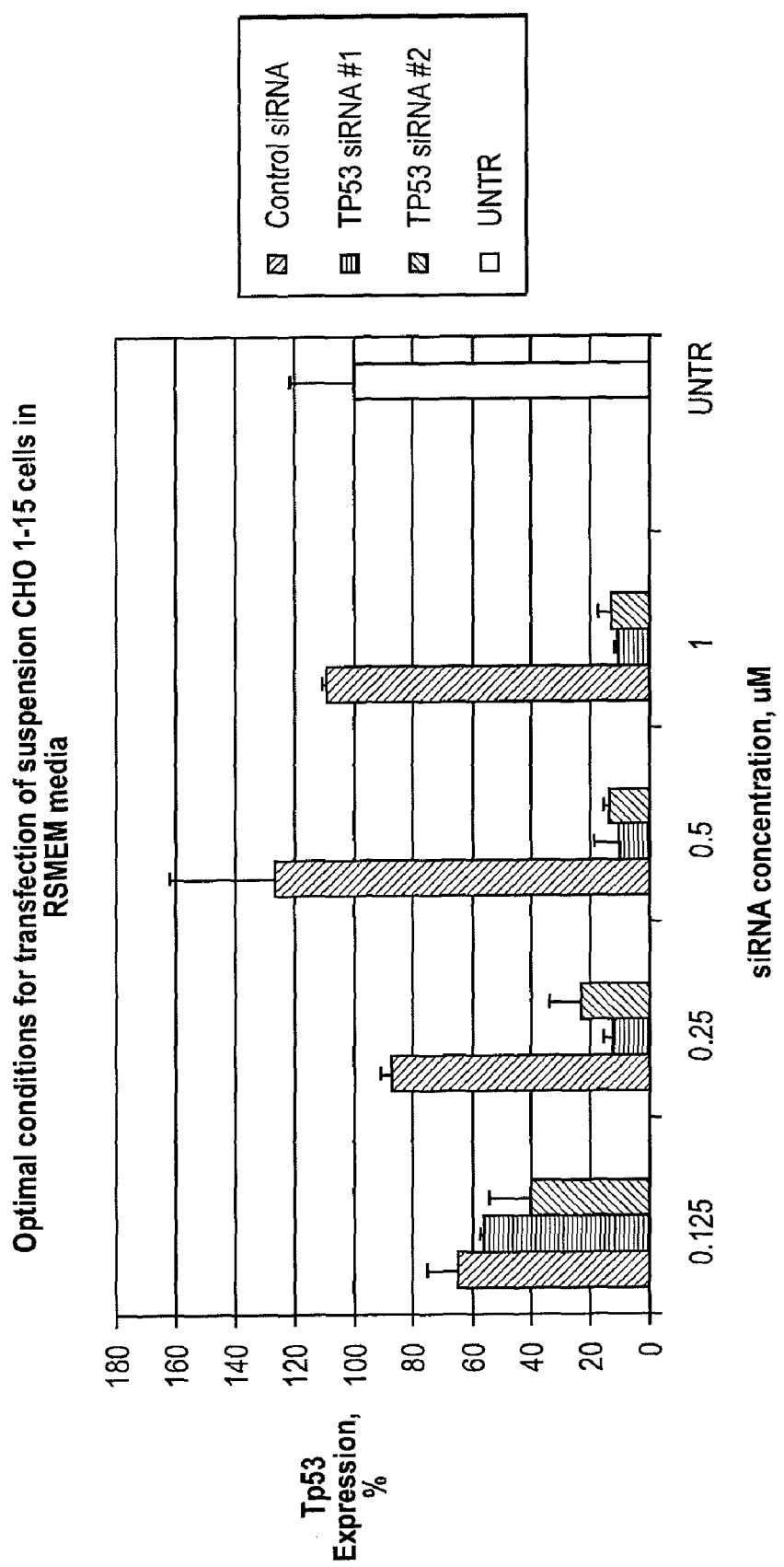

Results of these studies are shown in FIGS. 5A and 5B and demonstrate that gene knockdown can be achieved in CHO cells using chol-siRNAs. Using the CDM4-CHO serum free media (5 K cells plated per well) chol-siRNA #1 provided nearly 70% knockdown of TP53 at 1 micromolar concentrations. The chol-siRNA #2 provided superior performance, giving greater that 85% knockdown at both the 0.5 and 1.0 micromolar concentrations. Chol-siRNA mediated gene knockdown in CHO cells was even better using the HyClone reduced serum media (RSMEM). Both of the chol-siRNAs induced greater than 80% gene knockdown at concentrations between 0.25 and 1.0 micromolar. Together these studies demonstrate that chol-siRNA are capable of knocking down gene expression in CHO cell lines.

Example 2

The ability of chol-siRNA to induce a desired phenotype in CHO cells was examined. To test whether chol-siRNA were capable of inducing a phenotype in CHO cells, gene silencing reagents carrying the chol-siRNA modification pattern of Example 1 were designed and synthesized in order to target three different genes associated with the apoptosis pathway (e.g., Bax, Bak, and Casp3 genes). The chol-siRNAs targeting the Bax gene, Bak gene, and Casp3 gene are shown in Table 2 above. The CHO 1-15 cells were then plated at 20,000 cells per well (96 well format) and then treated with 0.5 micromolar concentrations of each chol-siRNA (equimolar pools of 4 individual siRNAs) and control siRNA for 72 hours, where the chol-siRNA and control siRNA were provided in RSMEM media. At 72, 96, and 120 hours after the initiation of chol-siRNA treatment, the fraction of cells entering early apoptosis in each culture was assessed using an ApoOne assay (measures Caspase 3/7 activity, Promega).

Figure 6A:
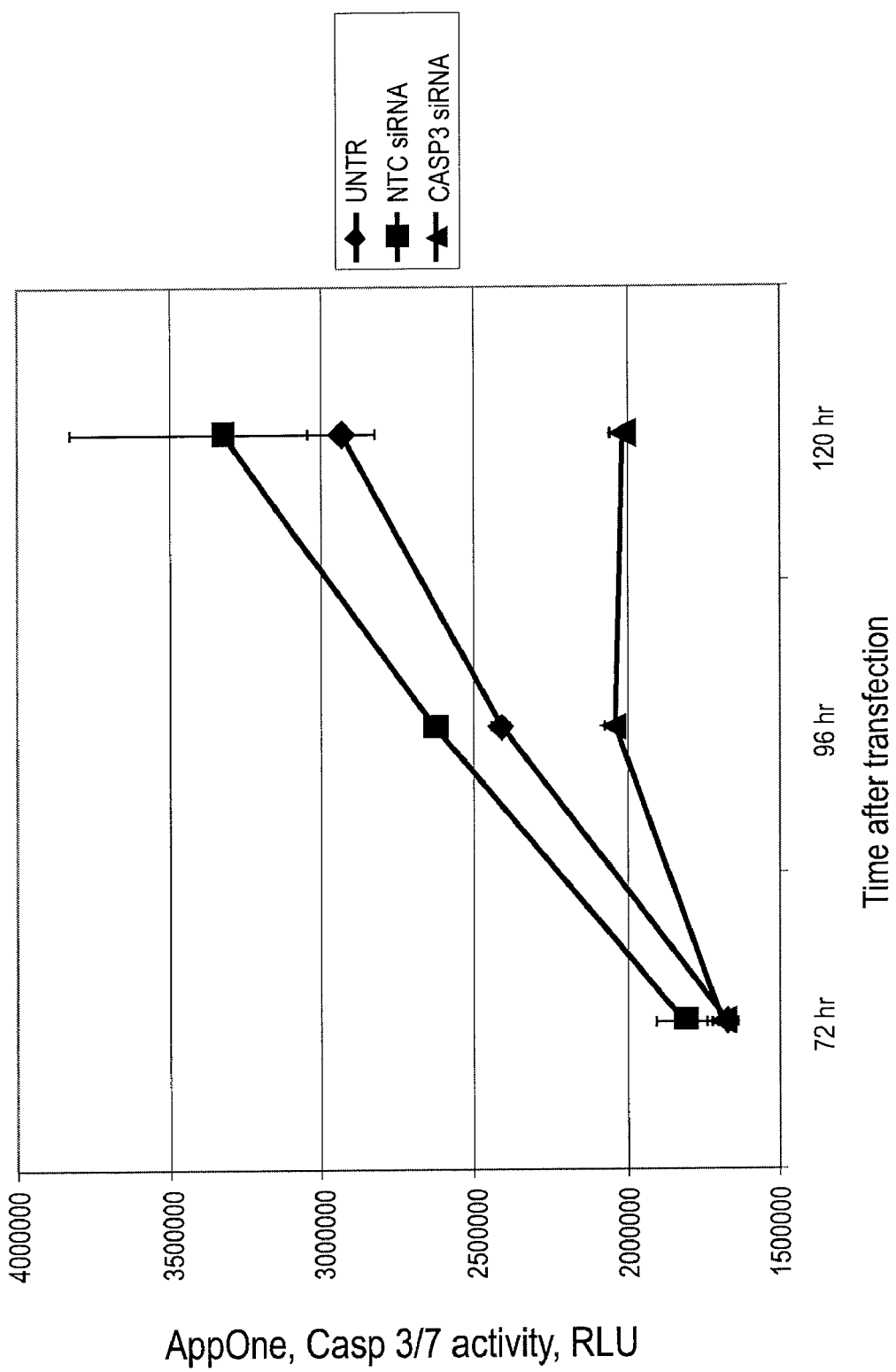
FIG. 6A includes a graph illustrating gene silencing in CHO cells with passively delivered siRNA are effective in silencing a target gene.

Results for the experiments are as follows: untreated CHO cultures as well as CHO cultures treated with non-targeting control siRNA show a steady rise in early apoptotic cells as judged by the ApoOne assay. Treatment of CHO cells with chol-siRNA targeting Bak or Bax did not significantly change the fraction of cells that enter early apoptosis (data not shown). In contrast, cells treated with chol-siRNA targeting Casp3 show a dramatic, dose-dependent reduction in the ApoOne readout (see FIGS. 6A and 6B). As shown, at 0.5 micromolar chol-siRNA concentrations, the ApoOne readout is 17 and 30% lower than untreated cells at the 96 and 120 hour time points, respectively. These findings demonstrate that chol-siRNA can induce desirable phenotypes in CHO cells.

Example 3

The knockdown of Casp3 using the chol-siRNA of Example 1 was investigated to determine if such a knockdown can enhance the production of human tissue plasminogen activator (tPA). Previous examples have shown that chol-siRNA can successfully knockdown gene expression in CHO cells, and chol-siRNA mediated gene knockdown can induce desirable phenotypes (i.e., preventing cells from entering early apoptosis). To determine whether chol-siRNA are capable of improving production of a biomolecule, we tested whether chol-siRNA targeting Casp3 for silencing can increase production of tPA. Specifically, Casp3-targeting chol-siRNA molecules were passively introduced into CHO 1-15 cells (0.5 uM) that expressed and secreted human recombinant tPA. At 144 hours post-treatment, samples of the culture media were removed and the concentration of tPA in the media was assessed by ELISA. The levels of tPA in media taken from untreated cultures (same cell density) was used as a control.

Figure 7:
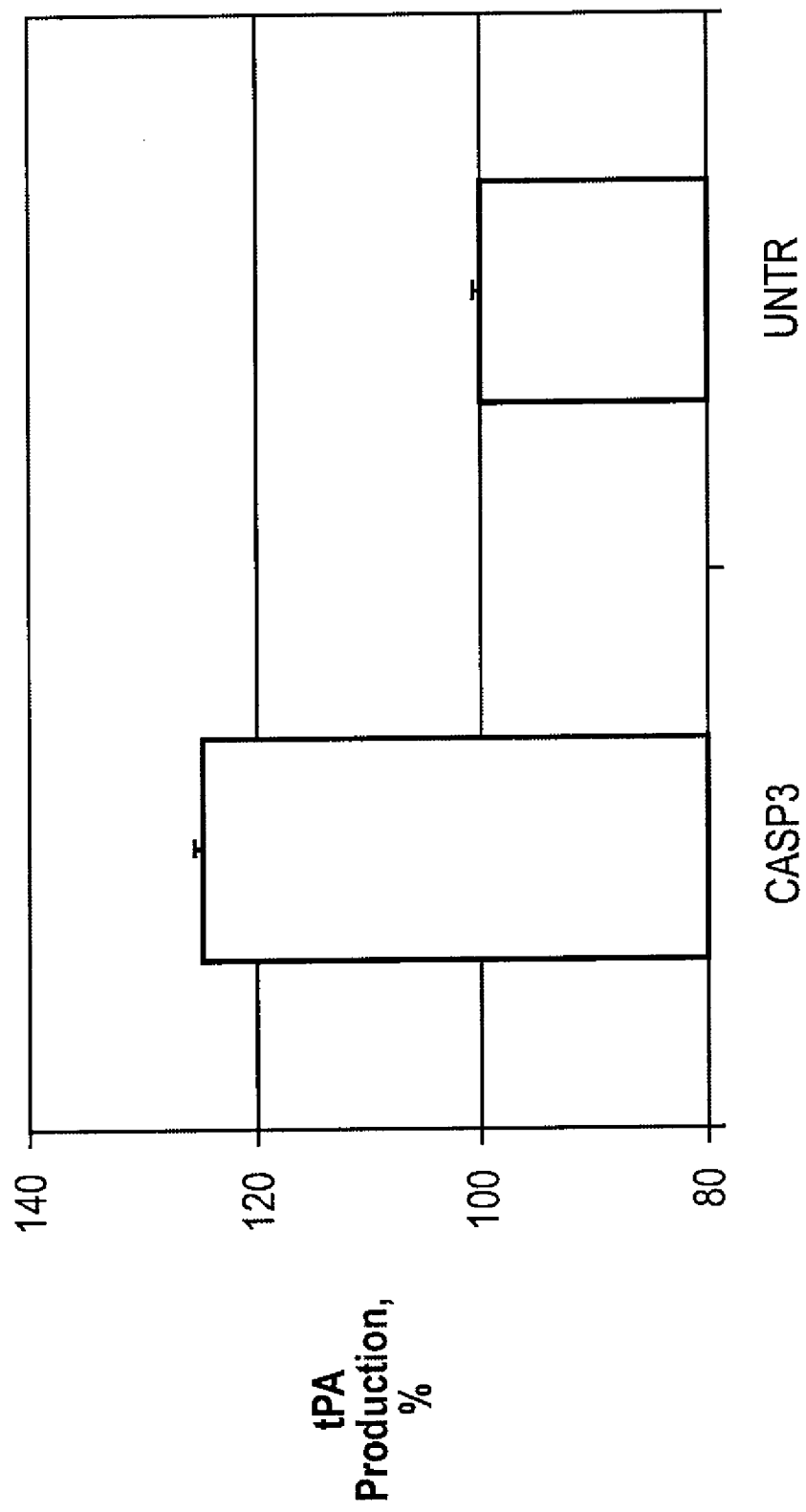
FIG. 7 shows a bar graph depicting the level of tPA production in cells that are untreated or treated with siRNA targeting Casp3 for silencing.

The results of these studies are presented in FIG. 7 and show that the amounts of tPA present in the chol-siRNA-treated culture media were 25.8% higher than in untreated cultures. These findings demonstrate that chol-siRNA silencing key genes associated with the modulation of apoptosis can significantly increase the amount of a desired bioproduct. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method for producing a protein-containing product from CHO cells, the method comprising:
   culturing recombinant host CHO cells containing nucleic acid encoding at least a portion of the protein-containing product;
   contacting the recombinant host CHO cell with a synthetic, chemically modified siRNA having a delivery facilitating conjugate linked to a polynucleotide of the siRNA, said contacting being under conditions in which the synthetic siRNA passively transfects the recombinant host CHO cell in an amount sufficient to inhibit expression of a first protein,
   wherein the synthetic, chemically modified siRNA includes:
      a sense strand having:
         2'-O-methyl modifications on the ultimate and penultimate nucleotides;
         2'-O-methyl modifications on each pyrimidine nucleotide; and
         a cholesterol or cholesterol derivative conjugate coupled to the 3' end of the sense strand through a linker having a 3-member to 8-member carbon chain; and
      an antisense strand having:
         2'-fluorine modifications on each pyrimidine nucleotide a 5' terminal phosphate;
         a U-U 3' overhang that includes phosphorothioate internucleotide linkages; and
         one of an A-A mismatch, a U-U mismatch, a C-C mismatch, or a G-G mismatch between nucleotide 6 from the 5' end of the sense strand and the opposite nucleotide on the antisense strand,
   wherein expression of the first protein decreases the production efficiency of the protein-containing product;
   incubating the recombinant host CHO cells with the synthetic siRNA under conditions that inhibit expression of the first protein;
   incubating the recombinant host CHO cells under conditions that express the protein-containing product; and
   recovering the protein-containing product.

2. The method of claim 1, wherein the delivery facilitating conjugate is a lipid.

3. The method of claim 2, wherein the lipid is cholesterol or derivative thereof.

4. The method of claim 1, further comprising:
   inhibiting expression of the first protein during a first portion of the step of incubating the recombinant host cell while the recombinant host cell is replicating; and
   expressing the protein-containing product during a second portion of incubating the recombinant host cell after the expression of the first protein has been inhibited.

5. The method of claim 1, wherein the first protein is the protein of the protein-containing product expressed at a time point unfavorable for producing a protein-containing product.

6. The method of claim 1, wherein the first protein is selected from at least one of the following:
   a vector protein that is deleterious to cell viability;
   a vector protein that is deleterious to production of the protein-containing product;
   a protein that is expressed at a particular stage of a bioprocess that is deleterious to the growth of the recombinant host cell;
   a protein that is expressed in Phase I of a bioprocess;
   a protein that is expressed in Phase II of a bioprocess;
   a protein that is expressed in Phase III of a bioprocess;
   a protein that modifies the protein-containing product into an undesired form;
   a protease; a glycosylase; a kinase;
   a phosphatase; a protein that post-translationally modifies the protein-containing product;
   a protein that is over-expressed; a protein that is highly expressed so as to be deleterious to the expression of the protein-containing product;
   a protein that causes degradation of the protein-containing product;
   a ubiqutinase;
   a protein that associates with the protein-containing product;
   a protein that has substantially the molecular weight of the protein-containing product;
   a protein that has substantially the isoelectric point of the protein-containing product;
   a protein that has substantially the purification properties of the protein-containing product;
   a protein that interferes with recovering the protein-containing product;
   a protein that co-elutes with the protein-containing product;
   a viral protein;
   a protein having an activity that introduces a substantial structural heterogeneity into the protein-containing product;
   a fucosyl transferase;
   a caspase;
   a calcium transporter; or
   CD16(Fc)(RIII).

7. The method of claim 1, wherein the synthetic siRNA contacts the recombinant host CHO cell prior to incubating the recombinant host cell in a bioreactor.

8. The method of claim 1, wherein the recombinant host CHO cell is incubated for a first time period in a bioreactor, is then contacted with the synthetic siRNA, and is then incubated for a second time period in a bioreactor.

9. The method of claim 1, further comprising:
   incubating the recombinant host CHO cell for a first time period in a bioreactor in the absence of the synthetic siRNA;
   contacting with the synthetic siRNA in a bioreactor; and
   incubating the recombinant host CHO cell for a second time period in a bioreactor.

10. The method of claim 1, further comprising inhibiting the production of the first protein so as to enhance bioproduction of the protein-containing product compared to when production of the first protein is not inhibited.

11. The method of claim 1, wherein the method comprises at least one of the following:
    inhibiting production of fucosyl transferase;
    inhibiting production of caspases to inhibit apoptosis;
    silencing cell cycle progression genes to inhibit cell proliferation;
    silencing pro-senescence genes to inhibit host cell death;
    silencing calcium transporter genes to limit cross links;
    silencing a gene encoding CD16(Fc)(RIII) to prohibit aggregation;
    silencing genes encoding factors that destabilize transcriptions and/or affect translation; or
    silencing genes encoding factors associated with glycosylation of proteins.

12. The method of claim 1, wherein the protein-containing product is recovered from the recombinant host CHO cell.

13. The method of claim 1, wherein the protein-containing product is exported from the recombinant host CHO cell to the surrounding media during the incubation of the recombinant host cell, and the protein-containing product is recovered from the surrounding media.

14. A method for producing a protein-containing product from a recombinant host cell, the method comprising:
  culturing the recombinant host cell containing nucleic acid encoding at least a portion of the protein-containing product;
  contacting the recombinant host cell with a synthetic, chemically modified siRNA having a delivery facilitating moiety linked to a polynucleotide of the siRNA, said contacting being under conditions in which the synthetic siRNA passively transfects the recombinant host cell in an amount sufficient to inhibit expression of a first protein,
    wherein the synthetic, chemically modified siRNA includes:
      a sense strand having:
        2'-O-methyl modifications on the ultimate and penultimate nucleotides;
        2'-O-methyl modifications on each pyrimidine nucleotide; and
        a cholesterol or cholesterol derivative conjugate coupled to the 3' end of the sense strand through a linker having a 3-member to 8-member carbon chain; and
      an antisense strand having:
        2'-fluorine modifications on each pyrimidine nucleotide a 5' terminal phosphate;
        a U-U 3' overhang that includes phosphorothioate internucleotide linkages; and
        one of an A-A mismatch, a U-U mismatch, a C-C mismatch, or a G-G mismatch between nucleotide 6 from the 5' end of the sense strand and the opposite nucleotide on the antisense strand,
    wherein expression of the first protein decreases the production efficiency of the protein-containing product; incubating the recombinant host cell with the synthetic siRNA under conditions that inhibit expression of the first protein;
  incubating the recombinant host cell under conditions that express the protein-containing product; and
  recovering the protein-containing product.

15. The method of claim 14 wherein the recombinant host cell is a CHO cell.

16. The method of claim 14 wherein the delivery facilitating moiety conjugate is a lipid.

17. The method of claim 16 wherein the lipid is cholesterol or derivative thereof.

* * * * *

SEQUENCE LISTING

```
<160> NUMBER OF SEQ ID NOS: 28

<210> SEQ ID NO 1
<211> LENGTH: 21
<212> TYPE: RNA
<213> ORGANISM: Cricetulus griseus

<400> SEQUENCE: 1
ugaccucgga ucuuaagggu u                                                    21

<210> SEQ ID NO 2
<211> LENGTH: 21
<212> TYPE: RNA
<213> ORGANISM: Cricetulus griseus

<400> SEQUENCE: 2
agcucuugaa acaucuugau u                                                    21

<210> SEQ ID NO 3
<211> LENGTH: 21
<212> TYPE: RNA
<213> ORGANISM: Cricetulus griseus

<400> SEQUENCE: 3
uauuccuucu ucaccauggu u                                                    21

<210> SEQ ID NO 4
<211> LENGTH: 21
<212> TYPE: RNA
<213> ORGANISM: Cricetulus griseus

<400> SEQUENCE: 4
uacuguuuca gcauggcacu u                                                    21

<210> SEQ ID NO 5
<211> LENGTH: 21
<212> TYPE: RNA
<213> ORGANISM: Cricetulus griseus
```

```
<400> SEQUENCE: 5
uuauuauuaa cuauuauacu u                                              21

<210> SEQ ID NO 6
<211> LENGTH: 21
<212> TYPE: RNA
<213> ORGANISM: Cricetulus griseus

<400> SEQUENCE: 6
auaaauucaa gcuugucggu u                                              21

<210> SEQ ID NO 7
<211> LENGTH: 21
<212> TYPE: RNA
<213> ORGANISM: Cricetulus griseus

<400> SEQUENCE: 7
ggucucuugu uccugauggu u                                              21

<210> SEQ ID NO 8
<211> LENGTH: 21
<212> TYPE: RNA
<213> ORGANISM: Cricetulus griseus

<400> SEQUENCE: 8
agcaaauugu ccaucucggu u                                              21

<210> SEQ ID NO 9
<211> LENGTH: 21
<212> TYPE: RNA
<213> ORGANISM: Cricetulus griseus

<400> SEQUENCE: 9
ucuuaaauag gcuggaggcu u                                              21

<210> SEQ ID NO 10
<211> LENGTH: 21
<212> TYPE: RNA
<213> ORGANISM: Cricetulus griseus

<400> SEQUENCE: 10
gaaaacauag cuucgaaagu u                                              21

<210> SEQ ID NO 11
<211> LENGTH: 21
<212> TYPE: RNA
<213> ORGANISM: Cricetulus griseus

<400> SEQUENCE: 11
uagcaaagua gaaaagggcu u                                              21

<210> SEQ ID NO 12
<211> LENGTH: 21
<212> TYPE: RNA
<213> ORGANISM: Cricetulus griseus

<400> SEQUENCE: 12
uguucuucca gaucgugagu u                                              21

<210> SEQ ID NO 13
<211> LENGTH: 21
<212> TYPE: RNA
<213> ORGANISM: Cricetulus griseus
```

-continued

```
<400> SEQUENCE: 13
ucaacuucuu gguagacggu u                                              21

<210> SEQ ID NO 14
<211> LENGTH: 21
<212> TYPE: RNA
<213> ORGANISM: Cricetulus griseus

<400> SEQUENCE: 14
uccacauuag caaucauccu u                                              21

<210> SEQ ID NO 15
<211> LENGTH: 21
<212> TYPE: RNA
<213> ORGANISM: Cricetulus griseus

<400> SEQUENCE: 15
ugguuuacau gucgacuaau u                                              21

<210> SEQ ID NO 16
<211> LENGTH: 21
<212> TYPE: RNA
<213> ORGANISM: Cricetulus griseus

<400> SEQUENCE: 16
ugguuuacau guuuucugau u                                              21

<210> SEQ ID NO 17
<211> LENGTH: 21
<212> TYPE: RNA
<213> ORGANISM: Cricetulus griseus

<400> SEQUENCE: 17
ugguuuacau guuuuccuau u                                              21

<210> SEQ ID NO 18
<211> LENGTH: 21
<212> TYPE: RNA
<213> ORGANISM: Cricetulus griseus

<400> SEQUENCE: 18
ugguuuacau guugugugau u                                              21

<210> SEQ ID NO 19
<211> LENGTH: 19
<212> TYPE: RNA
<213> ORGANISM: Cricetulus griseus

<400> SEQUENCE: 19
cccuuuagau ccgagguca                                                 19

<210> SEQ ID NO 20
<211> LENGTH: 19
<212> TYPE: RNA
<213> ORGANISM: Cricetulus griseus

<400> SEQUENCE: 20
ucaaguuguu ucaagagcu                                                 19

<210> SEQ ID NO 21
<211> LENGTH: 19
<212> TYPE: RNA
<213> ORGANISM: Cricetulus griseus
```

```
<400> SEQUENCE: 21
ccaugcugaa gaaggaaua                                              19

<210> SEQ ID NO 22
<211> LENGTH: 19
<212> TYPE: RNA
<213> ORGANISM: Cricetulus griseus

<400> SEQUENCE: 22
gugccuugcu gaaacagua                                              19

<210> SEQ ID NO 23
<211> LENGTH: 19
<212> TYPE: RNA
<213> ORGANISM: Cricetulus griseus

<400> SEQUENCE: 23
guauauuagu uaauaauaa                                              19

<210> SEQ ID NO 24
<211> LENGTH: 19
<212> TYPE: RNA
<213> ORGANISM: Cricetulus griseus

<400> SEQUENCE: 24
ccgacuagcu ugaauuuau                                              19

<210> SEQ ID NO 25
<211> LENGTH: 19
<212> TYPE: RNA
<213> ORGANISM: Cricetulus griseus

<400> SEQUENCE: 25
uuaguggaca uguaaacca                                              19

<210> SEQ ID NO 26
<211> LENGTH: 19
<212> TYPE: RNA
<213> ORGANISM: Cricetulus griseus

<400> SEQUENCE: 26
ucagauaaca uguaaacca                                              19

<210> SEQ ID NO 27
<211> LENGTH: 19
<212> TYPE: RNA
<213> ORGANISM: Cricetulus griseus

<400> SEQUENCE: 27
uaggauaaca uguaaacca                                              19

<210> SEQ ID NO 28
<211> LENGTH: 19
<212> TYPE: RNA
<213> ORGANISM: Cricetulus griseus

<400> SEQUENCE: 28
ucacagaaca uguaaacca                                              19
```